United States Patent [19]

Fauchere et al.

[11] Patent Number: 5,371,071
[45] Date of Patent: Dec. 6, 1994

[54] PEPTIDE AND PSEUDOPEPTIDE COMPOUNDS WHICH ARE THERAPEUTICALLY ACTIVE IN THE BLOOD COAGULATION CASCADE

[75] Inventors: Jean-Luc Fauchere, Saint-Cloud; Christophe Thurieau, Boulogne sur Seine; Tony Verbeuren, Vernouillet; Joseph Paladino, Conflans Sainte Honorine, all of France

[73] Assignee: Adir et Compagnie, Courbevoie, France

[21] Appl. No.: 3,883

[22] Filed: Jan. 13, 1993

[30] Foreign Application Priority Data

Jan. 15, 1992 [FR] France .................. 92 00340

[51] Int. Cl.$^5$ .................. C07K 7/06; C07K 7/08; A61K 37/02
[52] U.S. Cl. .................. 514/14; 530/317; 530/327; 514/11
[58] Field of Search .................. 530/317, 327; 514/14, 514/11

[56] References Cited

PUBLICATIONS

Maragonore et al. "The Journal of Biological Chemistry" 264 (15) 8692–8698 (1989).
Naski et al. "The Journal of Biological Chemisty" 265(23) (1990) 13484–13489.
Dayhoff "Atlas of Protein Sequence and Structure" 1972 vol. 5, pp. 89–99.
Drugs of the Future 15, No. 3, 267–280 (1990).

*Primary Examiner*—Robert J. Hill, Jr.
*Assistant Examiner*—Carol A. Salata
*Attorney, Agent, or Firm*—Gordon W. Hueschen

[57] ABSTRACT

The invention relates to the compounds of formula (I):

$$X - A_1 - A_2 - A_3 - A_4 - A_5 - A_6 - A_7 - A_8 - A_9 - A_{10} - Y \quad (I)$$

in which X, $A_1$, $A_2$, $A_3$, $A_4$, $A_5$, $A_6$, $A_7$, $A_8$, $A_9$, $A_{10}$ and Y are as defined in the description.

Medicinal products.

7 Claims, No Drawings

PEPTIDE AND PSEUDOPEPTIDE COMPOUNDS WHICH ARE THERAPEUTICALLY ACTIVE IN THE BLOOD COAGULATION CASCADE

The present invention relates to new peptide and pseudopeptide compounds which are therapeutically active in the blood coagulation cascade.

It is now widely known that, when the balance between procoagulant and anticoagulant factors in the blood is disturbed, the outcome can be the formation of a thrombus or blood clot. The development of a thrombosis is favored essentially by three main pathogenic factors, which are stasis or decrease in blood flow, hypercoagulability states and lesions of the endothelium of the vascular wall. To counter these pathogenic factors, it is hence appropriate to establish a treatment one of the main bases of which is the anticoagulant drug.

Anticoagulants are, in effect, usable in the treatment of acute venous thromboses, pulmonary embolism, arterial embolism of the extremities, arterial thromboses such as myocardial infarction and all other thromboembolic manifestations.

Among known anticoagulant agents, hirudin, which is a polypeptide containing 65 amino acids, is a specific inhibitor of thrombin, isolated from the salivary glands of the medicinal leech (Biochemistry 25, 4622-28, 1986).

Hirudin variants which are usable as a thrombin inhibitor have already been described. This applies, for example, to the compounds described in Patents EP 209,061 or EP 332,523. Moreover, synthetic analogs of hirudin fragments having anticoagulant properties have also been described; this applies, for example, to the compounds claimed in Patents EP 276,014, EP 291,981, EP 291,982 and EP 333,356. Compared with the natural model, these shorter fragments (10 to 20 amino acids) offer the advantage of being more "manageable": in particular, their synthesis is simpler.

More recently, European Patent Application EP 0,372,503 has claimed peptides which are hirudin analogs in which a natural amino acid was replaced by a synthetic amino acid.

Application EP 0,443,598 claims peptides which are hirudin analogs in which a natural acid is replaced by a sulfonated or phosphonated compound.

Applications PCT 91/01,328 and EP 443,429 claim hirudin analogs in which the modifications cover both the introduction of unnatural amino acids and also the introduction of sulfonooxo- or phosphonooxoamino acids.

It is true that a peptide is a labile, readily hydrolyzable structure, and the aim of the modifications introduced in the prior art is to increase the stability of the analog synthesized.

All the compounds claimed in the prior art are, moreover, characterized by a general formula which is X-$A_4$-$A_B$-$A_C$-$A_D$-$A_E$-$A_F$-$A_G$-$A_H$-$A_I$-$A_J$-Y, where the radical X substituting the terminal amino residue is either a hydrogen atom or one or two alkyl groups having 1 to 6 carbon atoms, or one or two acyl groups having 2 to 10 carbon atoms, or a benzyloxycarbonyl or t-butyloxycarbonyl group.

The Applicant has now discovered compounds for which the nature of the radical X has been substantially modified. The compounds obtained have an antithrombotic, anticoagulant and/or platelet aggregation-inhibitory activity markedly greater than that of the closest compounds of the prior art.

Thus, the compounds of the invention have an anticoagulant activity at least 30 times as great as that of hirudin, equivalent to an activity at least three times as great as that of the closest compounds of the prior art.

This potency of activity combined with their high stability makes the compounds of the invention especially advantageous for therapeutic use.

The invention relates more especially to new peptide compounds corresponding to the general formula (I):

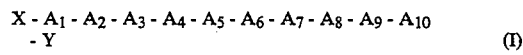

in which:

X represents the substituent of the terminal amino group of the peptide of formula (I) and represents a linear or branched guanidino($C_1$-$C_6$ acyl) group chosen from the groups

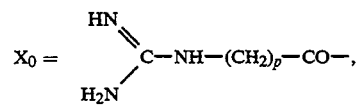

with $1 \leq p \leq 5$, a linear or branched guanidino($C_1$-$C_6$ alkyl) group, or any one of the following groups:

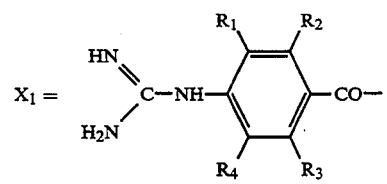

with $R_1$, $R_2$, $R_3$ and $R_4$, which may be identical or different, representing, independently of one another, a hydrogen atom, a linear or branched ($C_1$-$C_6$) alkyl group, a halogen atom, a trifluoromethyl group, a hydroxyl group, a linear or branched ($C_1$-$C_6$) alkoxy group, a thio group, a linear or branched ($C_1$-$C_6$) alkylthio group, a cyano group, a nitro group or a phenyloxy group,

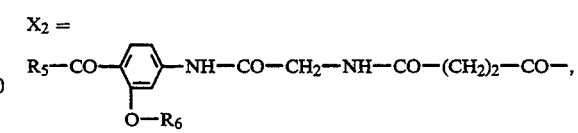

where $R_5$ represents a ($C_1$-$C_6$) lower alkoxy group or a hydroxyl group and where $R_6$ represents a hydrogen atom or a ($C_1$-$C_6$) lower acyl group, or

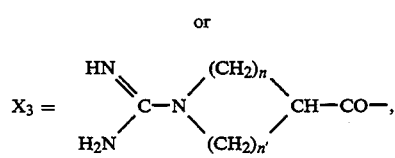

with n and n' being integers between 1 and 6, $A_1$ represents a bond or a peptide residue containing from 1 to 3 amino acids of any kind, which can include a residue $A_{11}$ of formula:

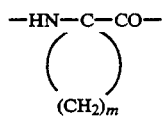

(with m being an integer between 2 and 7)

A$_2$ represents a bond or a phenylalanine (Phe), tyrosine (Tyr), isoleucine (Ile), norvaline (Nva), or 1,2,3,4-tetrahydroisoquinoline-3-carbonyl (Tic) residue, an α-aminobutyric acid (Abu) or glutamic acid (Glu) residue or an amino acid residue containing an aryl group, a residue A$_{11}$ or a residue A$_9$, A$_3$ represents a bond or a glutamic acid (Glu), aspartic acid (Asp), β-alanine (βAla), or tyrosine (Tyr) residue or a residue A$_{11}$, A$_4$ represents a bond or a glutamic acid (Glu), aspartic acid (Asp), proline (Pro), 2,3-diaminopropionic acid (Dpr), 2,4-diaminobutyric acid (Dab), ornithine (Orn), lysine (Lys), 2-azabicyclo[2.2.2]octane-3-carbonyl (Abo) or 2-azabicyclo[2.2.1]heptane-3-carbonyl (Abh) residue or a residue A$_{11}$, A$_5$ represents a bond or an isoleucine (Ile), norvaline (Nva), phenylalanine (Phe), proline (Pro), ornithine (Orn) or 2,3-diaminopropionic acid (Dpr) residue or a residue A$_{11}$, A$_6$ represents a proline (Pro), isoleucine (Ile), norvaline (Nva), phenylalanine (Phe), ornithine (Orn), 2-azabicyclo[2.2.2]octane-3-carbonyl (Abo), 2-azabicyclo [2.2.1]heptane-3-carbonyl (Abh), octahydroindole-2-carbonyl (Oic) or 3,4-dehydroproline (dhPro) residue, a residue A$_{11}$ or pipecolic acid (Pip), A$_7$ represents a glutamic acid (Glu) or aspartic acid (Asp) residue or a residue A$_{11}$, A$_8$ represents a glutamic acid (Glu), aspartic acid (Asp), 2,3-diaminopropionic acid (Dpr), 2,4-diaminobutyric acid (Dab) or β-alanine (βAla) residue or a residue A$_{11}$, A$_9$ represents a residue

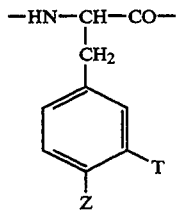

with Z or T, which are different, representing a hydrogen atom or an OPO$_3$H$_2$, PO$_3$H$_2$, CH$_2$CO$_2$H or OH group, on condition that, when Z represents OH, T is other than a hydrogen atom, A$_{10}$ represents a bond, a leucine (Leu), valine (Val), β-naphthylalanine (Nal), cyclohexylalanine (Cha), β-(2-thienyl)alanine (Thi), or octahydroindole-2-carbonyl (Oic) residue, a dipeptide residue such as Leu-Glu, Leu-Pro, Leu-βAla, Val-Glu, Nal-Glu, Cha-Glu, Thi-Glu, Oic-Glu, or leucine-(4-aminobutyric acid) (Leu-4Abu), a tripeptide residue such as Nal-Nal-Leu or a residue A$_{11}$ or a peptide fragment containing from 1 to 3 residues of any amino acid, Y represents the substituent on the terminal carbonyl group of the peptide of formula (I) and represents a hydroxyl group, a linear or branched (C$_1$-C$_6$) alkoxy group or an amino group which is itself optionally substituted with one or two linear or branched (C$_1$-C$_6$) alkyl groups, or alternatively the terminal carboxyl group of the peptide of formula (I) is reduced to the corresponding alcohol (ol), (—CH$_2$OH group), on the understanding that aryl group is understood to mean phenyl or naphthyl, it being possible for the compound of formula I optionally to include:

a pseudopeptide bond such as —CH$_2$—NH—, —CH$_2$—S—, —CH$_2$—SO—, —CH$_2$—SO$_2$—, —NH—CO—, or —CH=CH— replacing a peptide bond —CO—NH—, and/or a cyclization not involving cysteine between the side chains of two amino acids, or between a terminal amino group and a side chain or an amino acid, or between a terminal carboxyl group and a side chain of an amino acid, or between a terminal amino group and a terminal carboxyl group, and their addition salts with a pharmaceutically acceptable acid or base, each amino acid of the peptide sequence being optically pure and the α carbon of each amino acid having the D or L configuration.

Among pharmaceutically acceptable acids, there may be mentioned, without implied limitation, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric acids, and the like.

Among pharmaceutically acceptable bases, there may be mentioned, without implied limitation, sodium hydroxide, potassium hydroxide, triethylamine, tert-butylamine, and the like.

The expression "any amino acid" used in the present application includes both natural amino acids and so-called non-proteinogenous amino acids which are commonly used by a person skilled in the art in the synthesis of synthetic analogs of natural peptides.

Among natural amino acids, there may be mentioned, as an example and without implied limitation, glycine, alanine, valine, leucine, isoleucine, serine, methionine, threonine, phenylalanine, tyrosine, tryptophan, cysteine, proline, histidine, aspartic acid, asparagine, glutamine, glutamic acid, arginine, ornithine and lysine.

Among non-proteinogenous amino acids, there may be mentioned, as an example and without implied limitation, norleucine, norvaline, alloisoleucine, homoarginine, thiaproline, dehydroproline, hydroxyproline, homoserine, cyclohexylglycine, phenylglycine, amino-n-butyric acid, cyclohexylalanine, aminophenylbutyric acid, phenylalanines mono-, di- or trisubstituted on the phenyl group at the ortho, meta or para position with group(s) chosen from (C$_1$-C$_6$) alkyl, (C$_1$-C$_6$) alkoxy, halogen, trifluoromethyl, nitro, amino, mono- or di(C$_1$-C$_6$ alkyl)amino or alternatively a methylenedioxy group, β-(2- and 3- thienyl)alanine, β-(2- and 3-furyl)alanine, β-(2-, 3- and 4-pyridyl)alanine, β-(2- and 3-benzothienyl)alanine, β-(1- and 2-naphthyl)alanine, O-alkyl derivatives of serine, threonine, and tyrosine, S-alkylcysteines, all amino acids of D configuration, isomers of natural amino acids of L configuration, and the like.

The invention also extends to the process for preparing the compounds of formula (I), which may be obtained by various methods such as sequential solid-phase synthesis, the synthesis of fragments and their coupling in solution, enzymatic synthesis and genetic synthesis by cloning and expression of genes in transformed bacteria, or by various combinations of these techniques.

The general methods of solid-phase peptide synthesis have been described by B. W. ERICKSON and R. B. MERRIFIELD ("The Proteins", Solid-Phase Peptide Synthesis, 3rd edition, 257-527, 1976).

The solid-phase synthesis may be carried out on an automated apparatus which performs in a repetitive and programmable manner deprotection, coupling and washing cycles needed for the sequential introduction of the amino acids into the peptide chain. The amino acid, preferably C-terminal, is attached to a resin conventionally used for the preparation of polypeptides, preferably a polystyrene crosslinked using 0.5 to 3.0% of divinylbenzene and equipped with activated residues such as chloromethylene or hydroxymethylene which enable the first amino acid to be attached covalently to the resin. The appropriate choice of resin enables a C-terminal carboxylic acid, amide or alcohol function to be attached.

The amino acids are then introduced one by one in the order determined by the operator. Each synthesis cycle corresponding to the introduction of an amino acid entails a deprotection, preferably N-terminal, of the peptide chain, successive washes designed to remove the reactants or to swell the resin, a coupling with activation of the amino acid and further washes. Each of these operations is followed by a filtration, accomplished by means of the presence of a glass sinter incorporated in the reactor in which the synthesis takes place.

The coupling reagents used are standard reagents of peptide synthesis, such as dicyclohexylcarbodiimide (DCC) and hydroxybenzotriazole (HOBT) or benzotriazol-1-yloxytris (dimethylamino)phosphonium hexafluorophosphate (BOP) or alternatively diphenylphosphoryl azide (DPPA).

Activation by mixed anhydride formation is also possible.

Each amino acid is introduced into the reactor in approximately four-fold excess with respect to the degree of substitution of the resin, and in an approximately equivalent amount with respect to the coupling agents. The coupling reaction may be checked at each step of the synthesis by the ninhydrin reaction test described by E. KAISER et al. (Analyt. Biochem., 34, 595, 1970).

After assembly of the peptide chain on the resin, treatment with a strong acid such as trifluoroacetic acid or hydrofluoric acid in the presence of anisole, ethanedithiol or 2-methylindole serves to separate the peptide from the resin and also to free the peptide, where appropriate, from its protective groups. The compound is then purified by standard purification techniques, in particular chromatographic techniques.

The partial or total cyclization of the compounds of the invention is carried out in solution, preferably via two selectively deprotected functions capable of forming a covalent bond such as an amide bond.

The peptides of the present invention may also be obtained by the coupling in solution of selectively protected peptide fragments, which may be prepared either on a solid phase or in solution. The use of protective groups and the means of taking advantage of their differential stability are similar to the solid-phase methods, except for the attachment of the peptide chain to the resin. The C-terminal carboxyl group is protected, for example, by a methyl ester or an amide function. The methods of activation during coupling are also similar to those employed in solid-phase synthesis.

The synthesis of peptides containing pseudopeptide bonds such as $-CH_2-NH-$, $-CH_2-S-$, $-CH_2-SO-$, $-CH_2-SO_2-$, $-NH-CO-$ or $-CH=CH-$ is performed either by solution methods or in a combined procedure with solid-phase synthesis using standard methods of organic chemistry. Thus, for example, the introduction of the $-CH_2-NH-$ bond is accomplished by preparing in solution the aldehyde Fmoc-NH-CHR-CHO according to the technique described by FEHRENTZ and CASTRO (Synthesis, 676-678, 1983) and condensing it with the growing peptide chain, either on a solid phase according to the technique described by SASAKI and COY (Peptides, 8, 119-121, 1988), or in solution.

The compounds of formula (I) possess very advantageous pharmacological properties.

They are endowed with anticoagulant and antithrombotic properties, and may thus be used to prevent post-thromboembolic complications by dissolution of the clots or as agents for preventing extension of the thrombotic process, using them as direct- and rapid-acting anticoagulants. Their properties of inhibition of the thrombin-mediated platelet activation pathway enable their use to be envisaged as an inhibitor of the steps of interaction of blood platelets with the vascular wall, these steps being involved in the phenomena of thrombosis and atherosclerosis.

The subject of the present invention is also pharmaceutical compositions containing as active principle at least one compound of general formula (I) or one of its addition salts with a pharmaceutically acceptable acid or base, alone or in combination with one or more non-toxic, inert excipients or vehicles.

Among the pharmaceutical compositions according to the invention, there may be mentioned, more especially, those which are suitable for oral, parenteral or nasal administration, simple or sugar-coated tablets, sublingual tablets, sachets, packets, hard gelatin capsules, preparations to be placed under the tongue, troches, suppositories, creams, ointments, skin gels, aerosols, ampoules containing preparations to be swallowed or injected, and the like.

The dosage varies according to the patient's age and weight, nature and severity of the affliction and also the administration route.

The latter can be oral, nasal, rectal or parental. Generally speaking, the dosage ranges between 0.05 and 30 mg for a treatment administered in one or several doses per 24 hours.

The examples which follow illustrate the invention and in no way limit it.

In the examples below, the amino acids whose abbreviations begin with a capital letter are of the L configuration. The amino acids whose abbreviations begin with a lower-case letter are of the D configuration.

The amino acid designated Abo is of the 3S configuration.

The amino acid designated Oic is of the 2S,3aS,7aS configuration.

The symbol G represents the 4-guanidinobenzoyl radical:

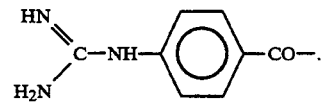

Tyr(mPO3H2) represents the residue:

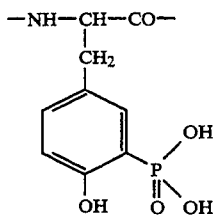

Tyr(pPO3H2) represents the residue:

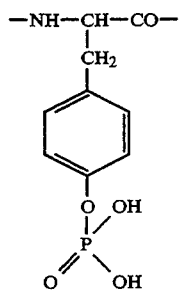

Phe(pPO3H2) represents the residue:

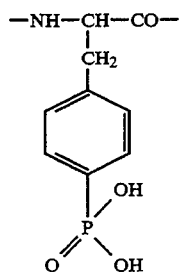

Phe(pCH2CO2H) represents the residue:

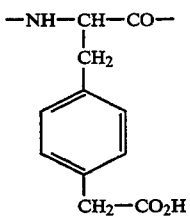

EXAMPLE 1

G-Gly-Asp-Phe-Glu-Abo-Ile-Pro-Glu-Glu-Tyr(-mPO3H2)-Leu-glu-OH trifluoroacetate (SEQ. ID NO: 1)

The compound of Example 1 is synthesized from 2 g of a resin substituted with 0.33 mmol/g of Fmoc-glu(OtBu)-OH and according to the following repetitive protocol:

| Operation no. | Function | Solvent/Reactant | Repetition/time |
|---|---|---|---|
| 1 | washing | DMF | 2 × 2 min |
| 2 | deprotection | 20% piperidine/DMF | 1 × 5 min |
| 3 | deprotection | 20% piperidine/DMF | 1 × 15 min |

-continued

| Operation no. | Function | Solvent/Reactant | Repetition/time |
|---|---|---|---|
| 4 | washing | DMF | 3 × 2 min |
| 5 | washing | dichloromethane | 3 × 2 min |
| 6 | coupling | activated protected amino acid | 1 × 90 min |
| 7 | washing | DMF | 3 × 2 min |
| 8 | washing | isopropyl alcohol | 3 × 2 min |
| 9 | washing | dichloromethane | 3 × 2 min |

Each of these operations, performed in 30 ml of solvent with agitation at room temperature, is followed by filtration through a glass sinter incorporated in the glass cell (reactor) in which the synthesis progresses. The filter retains the resin to which the growing peptide chain is attached.

The chosen protected amino acids were introduced in the following order: Fmoc-Leu-OH, Fmoc-Tyr[-(pOBzl),(mPO3(CH3)2]-OH, Fmoc-Glu(OtBu)-OH, Fmoc-Glu(OtBu)-OH, Fmoc-Pro-OH, Fmoc-Ile-OH, Fmoc-Abo-OH, Fmoc-Glu(OtBu)-OH, Fmoc-Phe-OH, Fmoc-Asp(OtBu)-OH, Fmoc-Gly-OH;

The activation for the purpose of coupling (operation 6) is obtained in each cycle by dissolving 4 equivalents (2.64 mmol) of the protected amino acid with 360 mg of HOBt in 30 ml of DMF, and then, after 30 minutes at room temperature, by adding 618 mg of DCC. This solution is then introduced immediately into the reaction cell with 10 ml of dichloromethane.

At the end of the nine cycles corresponding to the sequential attachment of eleven amino acids, and with C-terminal glutamic acid, a dodecapeptide protected on its side chains and attached to the resin has thereby been obtained. The condensation of the peptide chain with 4-guanidinobenzoic acid is performed in the presence of TBTU, HOBT and DIEA. The resin is then treated with a mixture of trifluoroacetic acid (18 ml), ethanedithiol (1 ml) and anisole (1 ml) for 90 minutes at room temperature. The filtrate and the solvents used for washing the resin are combined and evaporated to dryness. The product is precipitated in ether, filtered off and dried, then purified by preparative HPLC on a $C_{18}$ column (internal diameter: 47 mm, length: 300 mm) and lyophilized.

Analysis of the product obtained is carried out after decomposition of the latter into amino acids by hydrolysis in 6N hydrochloric acid for 18 hours at 110° C., and quantitative assay of the amino acids obtained by HPLC.

| | Asp | Gly | Glu | Leu | Phe | Pro | Tyr | Ile + Abo |
|---|---|---|---|---|---|---|---|---|
| calculated | 1 | 1 | 4 | 1 | 1 | 1 | 1 | 2 |
| found | 0.97 | 1.10 | 3.78 | 1.00 | 1.05 | 1.03 | 1.10 | 1.94 |

Mass spectrum (FAB): MR+, $m/_z = 1718$

The examples which follow were prepared using the procedure described in Example 1.

EXAMPLE 2

G-Acc-Asp-Phe-Glu-Abo-Ile-Pro-Glu-Glu-Tyr(-pPO3H2)-Leu-glu-OH trifluoroacetate (SEQ. ID NO. 2)

The resin substituted with Fmoc-Leu-glu(OtBu)-OH is condensed in the presence of piperidine, in the same manner as in Example 1, with Fmoc-Tyr[OPO$_3$(tBu)$_2$]-OH; this intermediate is obtained from Fmoc-Tyr-OH treated in three steps:
 a/ Carboxyl silylation using tert-butyldimethylsilyl chloride in the presence of N-methylmorpholine.
 b/ Phosphorylation using (Et)$_2$NP(OtBu)$_2$ in the presence of 1H-tetrazole.
 c/ Oxidation, deprotection using an aqueous solution of t-butyl hydroperoxide and sodium bisulfite (Na$_2$S$_2$O$_5$).

The intermediates are not isolated, and the final product Fmoc-Tyr[OPO$_3$(tBu)$_2$]-OH is purified in a conventional manner before condensation. At the end of the synthesis, paraguanidinobenzoic acid is condensed with the peptide chain previously obtained in the presence of BOP, HOBT and N-methylmorpholine.

EXAMPLE 3

G-Gly-Asp-Phe-Glu-Abo-Ile-Pro-Glu-Glu-Tyr(-pPO$_3$H$_2$)-Leu-glu-OH trifluoroacetate (SEQ. ID NO: 3)

| | Asp | Phe | Glu | Abo + Leu + Ile | Pro | Gly | Tyr |
|---|---|---|---|---|---|---|---|
| calculated | 1 | 1 | 4 | 3 | 1 | 1 | 1 |
| found | 1.03 | 1.05 | 4.01 | 2.80 | 1.01 | 1.05 | 1.05 |

Mass spectrum (FAB): MH+, m/z=1718

EXAMPLE 4

G-Acc-Asp-Phe-Glu-Abo-Ile-Pip-Glu-Glu-Tyr(-mPO$_3$H$_2$)-Leu-glu-OH trifluoroacetate (SEQ. ID NO: 4)

EXAMPLE 5

G-Acc-Asp-Phe-Glu-Abo-Ile-Pip-Glu-Glu-Tyr(-pPO$_3$H$_2$)-Leu-glu-OH trifluoroacetate (SEQ. ID NO: 5)

EXAMPLE 6

G-Gly-Asp-Tyr(pPO$_3$H$_2$)-Glu-Abo-Ile-Pro-Glu-Glu-Tyr(pPO$_3$H$_2$)-Leu-glu-OH trifluoroacetate (SEQ. ID NO: 6)

EXAMPLE 7

G-Gly-Asp-Phe-Glu-Abo-Ile-Oic-Glu-Glu-Tyr(-pPO$_3$H$_2$)-Leu-glu-OH trifluoroacetate (SEQ. ID NO: 7)

EXAMPLE 8

G-Acc-Asp-Phe-Glu-Abo-Ile-Oic-Glu-Glu-Tyr(-pPO$_3$H$_2$)-Leu-glu-OH trifluoroacetate (SEQ. ID NO: 8)

EXAMPLE 9

G-Acc-Asp-Tyr(pPO$_3$H$_2$)-Glu-Abo-Ile-Pro-Glu-Glu-Tyr(pPO$_3$H$_2$)-Leu-glu-OH trifluoroacetate (SEQ. ID NO: 9)

EXAMPLE 10

G-Acc-Asp-Tyr(pPO$_3$H$_2$)-Glu-Abo-Ile-Oic-Glu-Glu-Tyr(pPO$_3$H$_2$)-Leu-glu-OH trifluoroacetate (SEQ. ID NO: 10)

EXAMPLE 11

G-Gly-Asp-Tyr(pPO$_3$H$_2$)-Glu-Abo-Ile-Oic-Glu-Glu-Tyr(pPO$_3$H$_2$)-Leu-glu-OH trifluoroacetate (SEQ. ID NO: 11)

EXAMPLE 12

G-Gly-Asp-Tyr(pPO$_3$H$_2$)-Glu-Abo-Ile-Pro-Glu-Glu-Tyr(mPO$_3$H$_2$)-Leu-glu-OH trifluoroacetate (SEQ. ID NO: 12)

EXAMPLE 13

G-Gly-Asp-Tyr(pPO$_3$H$_2$)-Glu-Abo-Ile-Oic-Glu-Glu-Tyr(mPO$_3$H$_2$)-Leu-glu-OH trifluoroacetate (SEQ. ID NO: 13)

EXAMPLE 14

G-Acc-Asp-Tyr (pPO$_3$H$_2$)-Glu-Abo-Ile-Pro-Glu-Glu-Tyr(mPO$_3$H$_2$)-Leu-glu-OH trifluoroacetate (SEQ. ID NO: 14)

EXAMPLE 15

G-Acc-Asp-Phe-Glu-Abo-Ile-Pro-Glu-Glu-Phe(pPO$_3$H$_2$)-Leu-glu-OH trifluoroacetate (SEQ. ID NO: 15)

EXAMPLE 16

G-Gly-Asp-Phe-Glu-Abo-Ile-Oic-Glu-Glu-Phe(pPO$_3$H$_2$)-Leu-glu-OH trifluoroacetate (SEQ. ID NO: 16)

EXAMPLE 17

G-Gly-Asp-Phe-Glu-Abo-Ile-Pro-Glu-Glu-Phe(pPO$_3$H$_2$)-Leu-glu-OH trifluoroacetate (SEQ. ID NO: 17)

| | Asp | Glu | Gly | Pro | Phe | Ile + Abo | Leu |
|---|---|---|---|---|---|---|---|
| calculated | 1 | 4 | 1 | 1 | 1 | 2 | 1 |
| found | 0,98 | 3,92 | 1,02 | 0,99 | 1,00 | 2,02 | 0,97 |

Mass spectrum (FAB): MH+, m/z=1702

EXAMPLE 18

G-Acc-Asp-Phe-Glu-Abo-Ile-Oic-Glu-Glu-Phe(pPO$_3$H$_2$)-Leu-glu-OH trifluoroacetate (SEQ. ID NO: 18)

EXAMPLE 19

G-Acc-Asp-Phe(pPO$_3$H$_2$)-Glu-Abo-Ile-Pro-Glu-Glu-Phe(pPO$_3$H$_2$)-Leu-glu-OH trifluoroacetate (SEQ. ID NO: 19)

EXAMPLE 20

G-Acc-Asp-Phe(pPO$_3$H$_2$)-Glu-Abo-Ile-Oic-Glu-Glu-Phe(pPO$_3$H$_2$)-Leu-glu-OH trifluoroacetate (SEQ. ID NO: 20)

EXAMPLE 21

G-Gly-Asp-Phe(pPO$_3$H$_2$)-Glu-Abo-Ile-Oic-Glu-Glu-Phe(pPO$_3$H$_2$)-Leu-glu-OH trifluoroacetate (SEQ. ID NO: 21)

EXAMPLE 22

X$_0$-Gly-Asp-Tyr-Glu-Abo-Ile-Pro-Glu-Glu-Tyr(-pPO$_3$H$_2$)-Leu-glu-OH trifluoroacetate (SEQ. ID NO: 22) with, for X$_0$: p=1

EXAMPLE 23

$X_0$-Gly-Asp-Tyr-Glu-Abo-Ile-Oic-Glu-Glu-Tyr(-ppO$_3$H$_2$)-Leu-glu-OH trifluoroacetate (SEQ. ID NO: 23) with, for $X_0$: p=1

EXAMPLE 24

$X_0$-Acc-Asp-Tyr-Glu-Abo-Ile-Pro-Glu-Glu-Tyr(-pPO$_3$H$_2$)-Leu-glu-OH trifluoroacetate (SEQ. ID NO: 24) with, for $X_0$: p=1

EXAMPLE 25

$X_2$-Gly-Asp-Phe-Glu-Abo-Ile-Pip-Glu-Glu-Tyr(-mPO$_3$H$_2$)-Leu-OH trifluoroacetate (SEQ. ID NO: 25) with, for $X_2$: $R_5$=OH and $R_6$=H

EXAMPLE 26

$X_3$-Gly-Asp-Phe-Glu-Abo-Ile-Pro-Glu-Glu-Tyr(-mPO$_3$H$_2$)-Leu-glu-OH trifluoroacetate (SEQ. ID NO: 26) with, for $X_3$: n=n'=2

EXAMPLE 27

G-Gly-Asp-Phe-Glu-Abo-Ile-Abo-Glu-Glu-Tyr(-mPO$_3$H$_2$)-Leu-$\beta$Ala-OH trifluoroacetate (SEQ. ID NO: 27)

EXAMPLE 28

G-Gly-Asp-Phe-Glu-Abo-Ile-Pip-Glu-Glu-Tyr(-mPO$_3$H$_2$)-Leu-4Abu-OH trifluoroacetate (SEQ. ID NO: 28)

EXAMPLE 29

G-Phe-Glu-Abo-Ile-Pro-Glu-Glu-Tyr(mPO$_3$H$_2$)-Leu-glu-OH trifluoroacetate (SEQ. ID NO: 29)

EXAMPLE 30

G-Glu-Abo-Ile-Pro-Glu-Glu-Tyr(mPO$_3$H$_2$)-Leu-glu-OH trifluoroacetate (SEQ. ID NO: 30)

EXAMPLE 31

G-Phe-Glu-Abo-Ile-Pro-Glu-Glu-Tyr(pPO$_3$H$_2$)-Leu-$\beta$Ala-OH trifluoroacetate (SEQ. ID NO: 31)

EXAMPLE 32

G-Phe-Glu-Abo-Ile-Pro-Glu-Glu-Phe(pPO$_3$H$_2$)-Leu-glu-OH trifluoroacetate (SEQ. ID NO: 32)

EXAMPLE 33

G-Acc-Asp-Phe-Glu-Abo-Ile-Pro-Glu-Glu-Phe(pCH$_2$CO$_2$H)-Leu-glu-OH trifluoroacetate (SEQ. ID NO: 33)

EXAMPLE 34

G-Gly-Asp-Phe-Glu-Abo-Ile-Pro-Glu-Glu-Phe(pCH$_2$CO$_2$H)-Leu-glu-OH trifluoroacetate (SEQ. ID NO: 34)

EXAMPLE 35

G-Gly-Asp-Phe-Glu-Abo-Ile-Pro-Glu-Glu-phe(pCH$_2$CO$_2$H)-Leu-glu-OH trifluoroacetate (SEQ. ID NO: 35)

EXAMPLE 36

G-Acc-Asp-Phe-Glu-Abo-Ile-Oic-Glu-Glu-Phe(pCH$_2$CO$_2$H)-Leu-glu-OH trifluoroacetate (SEQ. ID NO: 36)

EXAMPLE 37

G-Gly-Asp-Phe-Glu-Abo-Ile-Oic-Glu-Glu-Phe(pCH$_2$CO$_2$H)-Leu-glu-OH trifluoroacetate (SEQ. ID NO: 37)

EXAMPLE 38

G-Gly-Asp-Phe-Glu-Abo-Ile-Pip-Glu-Glu-Phe(pCH$_2$CO$_2$H)-Leu-glu-OH trifluoroacetate (SEQ. ID NO: 38)

EXAMPLE 39

$X_0$-Acc-Asp-Phe-Glu-Abo-Ile-Oic-Glu-Glu-Phe(pCH$_2$CO$_2$H)-Leu-glu-OH trifluoroacetate (SEQ. ID NO: 39) with, for $X_0$: p=1

EXAMPLE 40

$X_0$-Acc-Asp-Phe-Glu-Abo-Ile-Pip-Glu-Glu-Phe(pCH$_2$CO$_2$H)-Leu-glu-OH trifluoroacetate (SEQ. ID NO: 40) with, for $X_0$: p=1

EXAMPLE 41

$X_2$-Acc-Asp-Phe-Glu-Abo-Ile-Abo-Glu-Glu-Phe(pCH$_2$CO$_2$H)-Leu-glu-OH trifluoroacetate (SEQ. ID NO: 41) with, for $X_2$: $R_5$=OH, $R_6$=H

EXAMPLE 42

$X_3$-Acc-Asp-Phe-Glu-Abo-Ile-Abo-Glu-Glu-Phe(pCH$_2$CO$_2$H) -Leu-glu-OH trifluoroacetate (SEQ. ID NO: 42) with, for $X_3$: n=n'=2

EXAMPLE 43

$X_3$-Acc-Asp-Phe-Glu-Abo-Ile-Pip-Glu-Glu-Phe(pCH$_2$CO$_2$H)-Leu-glu-OH trifluoroacetate (SEQ. ID NO: 43) with, for $X_3$: n=2, n'=1

EXAMPLE 44

G-Acc-Asp-Phe-Glu-Abo-Ile-Pip-Glu-Glu-Phe(pCH$_2$CO$_2$H)-Leu-glu-(CH$_2$OH) trifluoroacetate (SEQ. ID NO: 44)

CH$_2$OH meaning that the terminal carboxyl group is reduced to the alcohol —CH$_2$OH.

PHARMACOLOGICAL STUDY OF THE COMPOUNDS OF THE INVENTION

EXAMPLE 45

Antithrombotic Activity

The model of experimental thrombosis used is that of a venous thrombosis induced in male Wistar rats by ligation of the inferior vena cava below the left renal vein.

The test animals are anesthetized by intraperitoneal administration of Brietal ® (methohexital sodium) at a dose of 1 ml/kg.

Ligation is then carried out. The test product is injected subcutaneously 2 hours later into the left subclavian region. 4 hours after this injection, the blood is withdrawn directly from within the heart, the vein is excised and the clot is recovered and then weighed after transfer to an oven at 37° C. for 12 hours.

The compounds of the invention were tested as a single dose of 250 µg/kg in comparison with unsulfated hirudin used as a reference compound.

The results of this test showed that the compounds of the invention permit a significantly larger decrease in the weight of the clot than that observed on injection of unsulfated hirudin.

EXAMPLE 46

Anticoagulant Activity, Measurement of the Thrombin Time

In the presence of a standard quantity of thrombin, a normal plasma coagulates in a defined and constant time, referred to as the thrombin time (TT). Any prolongation of this time reflects an abnormality in fibrin formation (coagulation).

Sprague-Dawley rats are anesthetized with pentobarbital sodium (60 mg/kg i.p.), the carotid artery is catheterized and blood samples are taken into trisodium citrate solution (0.109M). A platelet-poor plasma is obtained by centrifugation of the blood samples (3000 g, 15 min). The plasma may be stored for 8 hours at 20° C.

The thrombin time is obtained with Prest thrombin reagent and determined automatically using a coagulometer.

The antagonist or the solvent (10 μl) is added to the plasma (90 μl), and then incubated for 2 minutes at 37° C. 100 μl of thrombin are added while starting the chronometer.

Under our conditions, the TT values obtained in the control plasma are of the order of 30 seconds. The activity of an antagonist is evaluated by its capacity to prolong this thrombin time relative to the control.

Under these conditions, the compounds of the invention permit a prolongation of the thrombin time of 50-fold and more. This prolongation is at least 30 times as large as that obtained with unsulfated hirudin 55-65. These results are markedly better than those obtained with the compounds of the prior art.

EXAMPLE 47

Platelet Aggregation

In this test, the antithrombin activity of the antagonists is evaluated by measuring the inhibition of thrombin-induced platelet aggregation.

Rabbits (2-3 kg) are anesthetized with pentobarbital sodium (30 mg/kg i.v.). After cannulation of the left carotid artery, the blood is withdrawn into sodium citrate (0.109M) (1 vol of citrate to 9 vol of blood).

Platelet-rich plasma (PRP) is obtained by centrifugation (20° C.) at 250 g for 20 minutes, and platelet-poor plasma (PPP) by centrifugation at 1000 g for 10 minutes. The number of platelets is adjusted to between 300,000 and 350,000 pl/mm$^3$ by dilution in autologous PPP. The PRP is stored at the temperature of the room until the time of the test, and is used within 4 hours following withdrawal.

The PRP is centrifuged again (900 g, 15 minutes) and the platelets are washed in Tris-buffered saline solution containing gelatin (0.2%). The washed platelets (WP) are then resuspended in physiological solution and stored at the temperature of the room.

Platelet aggregation is carried out at 37° C. in siliconed glass tubes using an aggregometer. The PRP and the WP are stirred at 1000 rpm (revolutions per minute).

Thrombin is incubated for 3 minutes at 37° C. with the test substance (at different concentrations) or with the solvent in a volume of 50 μl. The WP (225 μl) are preincubated for 1 minute at 37° C. in a siliconed glass cell with stirring (1000 rpm). Aggregation is obtained by adding 25 μl of the solution containing thrombin and the test substance. The aggregating response is recorded over at least 5 minutes.

The intensity of platelet aggregation is established by taking the maximal amplitude of the aggregation plots, and is expressed as a percentage light transmission (% T). For each of the compounds tested, an IC$_{50}$ was determined.

The compounds of the invention greatly inhibit thrombin-induced platelet aggregation.

EXAMPLE 48

Measurement of Anticoagulant Activity Ex Vivo. Prothrombin time

OFA rats, fasted or otherwise, are anesthetized with pentobarbital (60 mg/kg i.p.). The carotid and the jugular are exposed and catheterized. The catheters are flushed with citrated (1/40) physiological solution. After installation of the catheters, a sample of 1.5 cm$^3$ of arterial blood is withdrawn into 0.109M citrate (1/9).

30 minutes later, the test product is admini-stered i.v. in a volume of 1 ml.

Arterial blood samples (1.5 ml) are then withdrawn at 1 min 30 sec, 3 min, 5 min, 15 min, 30 min and 60 min.

As each sample is withdrawn, 1.5 ml of citrated physiological solution is reinjected into the animal via the carotid.

The blood tubes are centrifuged for 15 min at 4000 rpm (preparation of plasma).

100 μl of plasma are incubated with 200 μl of neoplastin calcium. The time of onset of the coagulation phenomenon is measured.

The compounds of the invention, tested at doses of 4 to 16 mg/kg, increase the prothrombin time (PT) in a dose-dependent manner. Their effect is greater than that of unsulfated hirudin. In effect, they increase the PT significantly. Moreover, while the in vivo activity of hirudin is of short duration (30 minutes), the increase in PT noted with the compounds of the invention is still significant 60 minutes after their administration.

EXAMPLE 49

Pharmaceutical Compositions

Injectable solution: G-Gly-Asp-Phe-Glu-Abo-Ile-Pro-Glu-Glu-Tyr(mPO$_3$H$_2$)-Leu-glu-OH: 5 mg Distilled water for injections, QS: 25 ml

| Tablet: Preparation formula for 1000 tablets | |
|---|---|
| G—Gly—Asp—Phe—Glu—Abo—Ile—Pro—Glu—Glu—Tyr(mPO$_3$H$_2$)—Leu—glu—OH | 5 g |
| Wheat starch | 10 g |
| Maize starch | 10 g |
| Lactose | 60 g |
| Magnesium stearate | 2 g |
| Hydroxypropylcellulose | 2 g |

An additional coating will provide for gastroresistance of the pharmaceutical dosage form.

We claim:

1. A peptide compound selected from those of formula (I):

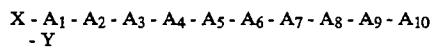 (I)

in which:

X represents a substituent of a terminal amino acid group of the peptide of formula (I) and represents:

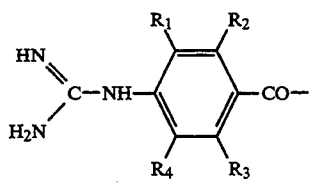

with $R_1$, $R_2$, $R_3$ and $R_4$, representing hydrogen, $A_1$ represents glycine-aspartic acid (Gly-Asp),
$A_2$ represents phenylalanine (Phe),
$A_3$ represents glutamic acid (Glu),
$A_4$ represents 2-azabicyclo[2.2.2]octane-3-carbonyl (Abo),
$A_5$ represents isoleucine (Ile),
$A_6$ represents a proline (Pro),
$A_7$ represents a glutamic acid (Glu),
$A_8$ represents a glutamic acid (Glu),
$A_9$ represents a residue

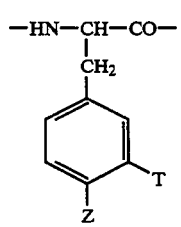

with Z or T, which are different, representing a hydrogen atom or an $PO_3H_2$, $CH_2CO_2H$, or OH group on condition that, when Z represents OH, T is other than a hydrogen atom,
$A_{10}$ represents a dipeptide residue Leu-Glu,
Y represents a substituent on a terminal carbonyl of the peptide of formula (I) and represents hydroxyl, and Pharmaceutically-acceptable acid or base addition salts thereof, each amino acid of the peptide sequence being optically pure and the α carbon of each amino acid having the D or L configuration.

2. A compound as claimed in claim 1, selected from those in which the residue $A_9$ is such that Z represents hydroxyl and T $PO_3H_2$, as well as pharmaceutically-acceptable acid or base addition salts thereof, each amino acid of the peptide sequence being optically pure and the α carbon of each amino acid having the D or L configuration.

3. A compound as claimed in claim 1, selected from those in which the residue $A_9$ is such that Z represents $PO_3H_2$ and T hydrogen, and pharmaceutically-acceptable acid or base addition salts thereof, each amino acid of the peptide sequence being optically pure and the α carbon of each amino acid having the D or L configuration.

4. A compound as claimed in claim 1, selected from those in which the residue $A_9$ is such that Z represents $CH_2CO_2H$ and T hydrogen, and pharmaceutically-acceptable acid or base addition salts thereof, each amino acid of the peptide sequence being optically pure and the α carbon of each amino acid having the D or L configuration.

5. A compound as claimed in claim 1 selected from G- Gly-Asp-Phe-Glu-Abo-Ile-Pro-Glu-Glu-Tyr(-mPO3H2)-Leu-glu -OH, where G represents the radical:

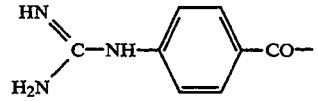

and Tyr(mPO3H2) represents:

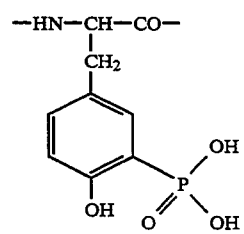

as well as pharmaceutically-acceptable acid or base addition salts thereof, each amino acid of the peptide sequence being optically pure and the α carbon of each amino acid having the D or L configuration.

6. A method for treating an animal or human living body afflicted with a disease requiring an anticoagulant comprising the step of administering to the living body an amount of a compound of claim 1 which is effective for alleviation of said disease.

7. A pharmaceutical composition useful as an anticoagulant comprising as active principle an effective anticoagulant amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,371,071                    Page 1 of 2

DATED     : December 6, 1994

INVENTOR(S) : Jean-Luc Fauchere, Christophe Thurieau, Tony Verbeuren, Joseph Paladino It is certified that error appears in the above-indentified patent and that said Letters Patent is hereby corrected as shown below:

```
Column  4, line  7; "-CH-" should read -- -CH2 --
Column  4, line  8; delete the "2" first occurrence.
Column  4, line  8; delete the "-N-" at the end of the line.
Column  4, line  9; insert "-N" at the beginning of the line.
Column  4, line 54; insert ")" after "furyl" and before the
     dash.
Column  4, line 55; delete the ")" at the beginning of the line.
Column  6, line  2; insert "2" at the end of the line before the
     dash.
Column  6, line  3; delete the "2" at the beginning of the line.
Column 10, line 23; delete the "(p" at the end of the line.
Column 10, line 24; insert the "(p" at the beginning of the line
Column 10, line 28; delete the "(p" at the end of the line.
Column 10, line 29; insert a "(p" at the beginning of the line.
Column 10, line 33; delete the "(p" at the end of the line.
Column 10, line 34; insert a "(p" at the beginning of the line.
Column 10, line 46; delete the "(p " at the end of the line Column 10, line 47; insert a "(p" at the beginning of the line.
```

UNITED STATES PATENT AND TRADEMARK OFFICE
CERTIFICATE OF CORRECTION

PATENT NO. : 5,371,071

DATED : December 6, 1994

INVENTOR(S) : Jean-Luc Fauchere, Christophe Thurieau, Tony Verbeuren, Joseph Paladino It is certified that error appears in the above-indentified patent and that said Letters Patent is hereby corrected as shown below:

Column 65, lines 24 and 25, the formula should all be on the same line to read as follows:

$$--X - A_1 - A_2 - A_3 - A_4 - A_5 - A_6 - A_7 - A_8 - A_9 - A_{10} - Y \text{ (I)}--.$$

Column 66, line 46; delete the space between "G-" and "Gly-"

Signed and Sealed this

Eighteenth Day of April, 1995

BRUCE LEHMAN

*Commissioner of Patents and Trademarks*

*Attest:*

*Attesting Officer*

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=G ( i x ) FEATURE:
        ( A ) NAME/KEY: Modified-site
        ( B ) LOCATION: 6
        ( D ) OTHER INFORMATION: /label=Abo ( i x ) FEATURE:
        ( A ) NAME/KEY: Modified-site
        ( B ) LOCATION: 11
        ( D ) OTHER INFORMATION: /note="Tyr(mPO3H2)"

( i x ) FEATURE:
        ( A ) NAME/KEY: Modified-site
        ( B ) LOCATION: 13
        ( D ) OTHER INFORMATION: /label=glu ( i x ) FEATURE:
        ( A ) NAME/KEY: Modified-site
        ( B ) LOCATION: 14
        ( D ) OTHER INFORMATION: /note="OH, trifluoroacetate"

( x i ) SEQUENCE DESCRIPTION: SEQ ID NO:1:

```
Xaa  Gly  Asp  Phe  Glu  Xaa  Ile  Pro  Glu  Glu  Xaa  Leu  Xaa  Xaa
 1                   5                        10
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=G ( i x ) FEATURE:
        ( A ) NAME/KEY: Modified-site
        ( B ) LOCATION: 2
        ( D ) OTHER INFORMATION: /label=Acc ( i x ) FEATURE:
        ( A ) NAME/KEY: Modified-site
        ( B ) LOCATION: 6
        ( D ) OTHER INFORMATION: /label=Abo ( i x ) FEATURE:
        ( A ) NAME/KEY: Modified-site
        ( B ) LOCATION: 11
        ( D ) OTHER INFORMATION: /note="Tyr(pPO3H2)"

( i x ) FEATURE:
        ( A ) NAME/KEY: Modified-site
        ( B ) LOCATION: 13
        ( D ) OTHER INFORMATION: /label=glu ( i x ) FEATURE:
        ( A ) NAME/KEY: Modified-site
        ( B ) LOCATION: 14
        ( D ) OTHER INFORMATION: /note="OH,trifluoroacetate"

-continued ( x i ) SEQUENCE DESCRIPTION: SEQ ID NO:2:

Xaa Xaa Asp Phe Glu Xaa Ile Pro Glu Glu Xaa Leu Xaa Xaa
1               5                   10

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=G ( i x ) FEATURE:
        ( A ) NAME/KEY: Modified-site
        ( B ) LOCATION: 6
        ( D ) OTHER INFORMATION: /label=Acc ( i x ) FEATURE:
        ( A ) NAME/KEY: Modified-site
        ( B ) LOCATION: 11
        ( D ) OTHER INFORMATION: /note="Tyr(pPO3H2)"

( i x ) FEATURE:
        ( A ) NAME/KEY: Modified-site
        ( B ) LOCATION: 13
        ( D ) OTHER INFORMATION: /label=glu ( i x ) FEATURE:
        ( A ) NAME/KEY: Modified-site
        ( B ) LOCATION: 14
        ( D ) OTHER INFORMATION: /note="OH,trifluoroacetate"

( x i ) SEQUENCE DESCRIPTION: SEQ ID NO:3:

Xaa Gly Asp Phe Glu Xaa Ile Pro Glu Glu Xaa Leu Xaa Xaa
1               5                   10

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=G ( i x ) FEATURE:
        ( A ) NAME/KEY: Modified-site
        ( B ) LOCATION: 2
        ( D ) OTHER INFORMATION: /label=Acc ( i x ) FEATURE:
        ( A ) NAME/KEY: Modified-site
        ( B ) LOCATION: 6
        ( D ) OTHER INFORMATION: /label=Abo ( i x ) FEATURE:
        ( A ) NAME/KEY: Modified-site
        ( B ) LOCATION: 8
        ( D ) OTHER INFORMATION: /label=Pip ( i x ) FEATURE:
        ( A ) NAME/KEY: Modified-site
        ( B ) LOCATION: 11
        ( D ) OTHER INFORMATION: /note="Tyr((mPO3H2)"

( i x ) FEATURE:
    ( A ) NAME/KEY: Modified-site
    ( B ) LOCATION: 13
    ( D ) OTHER INFORMATION: /label=glu ( i x ) FEATURE:
    ( A ) NAME/KEY: Modified-site
    ( B ) LOCATION: 14
    ( D ) OTHER INFORMATION: /note="OH,trifluoroacetate"

( x i ) SEQUENCE DESCRIPTION: SEQ ID NO:4:

```
Xaa Xaa Asp Phe Glu Xaa Ile Xaa Glu Glu Xaa Leu Xaa Xaa
1               5                   10
```

( 2 ) INFORMATION FOR SEQ ID NO:5:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=G ( i x ) FEATURE:
    ( A ) NAME/KEY: Modified-site
    ( B ) LOCATION: 2
    ( D ) OTHER INFORMATION: /label=Acc ( i x ) FEATURE:
    ( A ) NAME/KEY: Modified-site
    ( B ) LOCATION: 6
    ( D ) OTHER INFORMATION: /label=Abo ( i x ) FEATURE:
    ( A ) NAME/KEY: Modified-site
    ( B ) LOCATION: 8
    ( D ) OTHER INFORMATION: /label=Pip ( i x ) FEATURE:
    ( A ) NAME/KEY: Modified-site
    ( B ) LOCATION: 11
    ( D ) OTHER INFORMATION: /note="Tyr(pPO3H2)"

( i x ) FEATURE:
    ( A ) NAME/KEY: Modified-site
    ( B ) LOCATION: 13
    ( D ) OTHER INFORMATION: /label=glu ( i x ) FEATURE:
    ( A ) NAME/KEY: Modified-site
    ( B ) LOCATION: 14
    ( D ) OTHER INFORMATION: /note="OH,trifluoroacetate"

( x i ) SEQUENCE DESCRIPTION: SEQ ID NO:5:

```
Xaa Xaa Asp Phe Glu Xaa Ile Xaa Glu Glu Xaa Leu Xaa Xaa
1               5                   10
```

( 2 ) INFORMATION FOR SEQ ID NO:6:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=G ( i x ) FEATURE:
- ( A ) NAME/KEY: Modified-site
- ( B ) LOCATION: 4
- ( D ) OTHER INFORMATION: /note="Tyr(pPO3H2)"

( i x ) FEATURE:
- ( A ) NAME/KEY: Modified-site
- ( B ) LOCATION: 6
- ( D ) OTHER INFORMATION: /label=Abo ( i x ) FEATURE:
- ( A ) NAME/KEY: Modified-site
- ( B ) LOCATION: 11
- ( D ) OTHER INFORMATION: /note="same as b"

( i x ) FEATURE:
- ( A ) NAME/KEY: Modified-site
- ( B ) LOCATION: 13
- ( D ) OTHER INFORMATION: /label=glu ( i x ) FEATURE:
- ( A ) NAME/KEY: Modified-site
- ( B ) LOCATION: 14
- ( D ) OTHER INFORMATION: /note="OH,trifluoroacetate"

( x i ) SEQUENCE DESCRIPTION: SEQ ID NO:6:

```
Xaa Gly Asp Xaa Glu Xaa Ile Pro Glu Glu Xaa Leu Xaa Xaa
 1               5                   10
```

( 2 ) INFORMATION FOR SEQ ID NO:7:

( i ) SEQUENCE CHARACTERISTICS:
- ( A ) LENGTH: 14 amino acids
- ( B ) TYPE: amino acid
- ( C ) STRANDEDNESS: single
- ( D ) TOPOLOGY: linear ( i i ) MOLECULE TYPE: peptide ( i x ) FEATURE:
- ( A ) NAME/KEY: Modified-site
- ( B ) LOCATION: 1
- ( D ) OTHER INFORMATION: /label=G ( i x ) FEATURE:
- ( A ) NAME/KEY: Modified-site
- ( B ) LOCATION: 6
- ( D ) OTHER INFORMATION: /label=Abo ( i x ) FEATURE:
- ( A ) NAME/KEY: Modified-site
- ( B ) LOCATION: 8
- ( D ) OTHER INFORMATION: /label=Oic ( i x ) FEATURE:
- ( A ) NAME/KEY: Modified-site
- ( B ) LOCATION: 11
- ( D ) OTHER INFORMATION: /note="Tyr(pPO3H2)"

( i x ) FEATURE:
- ( A ) NAME/KEY: Modified-site
- ( B ) LOCATION: 13
- ( D ) OTHER INFORMATION: /label=glu ( i x ) FEATURE:
- ( A ) NAME/KEY: Modified-site
- ( B ) LOCATION: 14
- ( D ) OTHER INFORMATION: /note="OH,trifluoroacetate"

( x i ) SEQUENCE DESCRIPTION: SEQ ID NO:7:

```
Xaa Gly Asp Phe Glu Xaa Ile Xaa Glu Glu Xaa Leu Xaa Xaa
 1               5                   10
```

( 2 ) INFORMATION FOR SEQ ID NO:8:

( i ) SEQUENCE CHARACTERISTICS:
- ( A ) LENGTH: 14 amino acids (B) TYPE: amino acid
(C) STRANDEDNESS: single
(D) TOPOLOGY: linear (ii) MOLECULE TYPE: peptide (ix) FEATURE:
  (A) NAME/KEY: Modified-site
  (B) LOCATION: 1
  (D) OTHER INFORMATION: /label=G (ix) FEATURE:
  (A) NAME/KEY: Modified-site
  (B) LOCATION: 2
  (D) OTHER INFORMATION: /label=Acc (ix) FEATURE:
  (A) NAME/KEY: Modified-site
  (B) LOCATION: 6
  (D) OTHER INFORMATION: /label=Abo (ix) FEATURE:
  (A) NAME/KEY: Modified-site
  (B) LOCATION: 8
  (D) OTHER INFORMATION: /label=Oic (ix) FEATURE:
  (A) NAME/KEY: Modified-site
  (B) LOCATION: 11
  (D) OTHER INFORMATION: /note="Tyr(pPO3H2)"

(ix) FEATURE:
  (A) NAME/KEY: Modified-site
  (B) LOCATION: 13
  (D) OTHER INFORMATION: /label=glu (ix) FEATURE:
  (A) NAME/KEY: Modified-site
  (B) LOCATION: 14
  (D) OTHER INFORMATION: /note="OH,trifluoroacetate"

(xi) SEQUENCE DESCRIPTION: SEQ ID NO:8:

Xaa Xaa Asp Phe Glu Xaa Ile Xaa Glu Glu Xaa Leu Xaa Xaa
1               5                   10

(2) INFORMATION FOR SEQ ID NO:9:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=G (ix) FEATURE:
    (A) NAME/KEY: Modified-site
    (B) LOCATION: 2
    (D) OTHER INFORMATION: /label=Acc (ix) FEATURE:
    (A) NAME/KEY: Modified-site
    (B) LOCATION: 4
    (D) OTHER INFORMATION: /note="Tyr(pPO3H2)"

(ix) FEATURE:
    (A) NAME/KEY: Modified-site
    (B) LOCATION: 6
    (D) OTHER INFORMATION: /label=Abo (ix) FEATURE:
    (A) NAME/KEY: Modified-site
    (B) LOCATION: 11
    (D) OTHER INFORMATION: /note="Tyr(pPO3H2)"

( i x ) FEATURE:
  ( A ) NAME/KEY: Modified-site
  ( B ) LOCATION: 13
  ( D ) OTHER INFORMATION: /label=glu ( i x ) FEATURE:
  ( A ) NAME/KEY: Modified-site
  ( B ) LOCATION: 14
  ( D ) OTHER INFORMATION: /note="OH,trifluoroacetate"

( x i ) SEQUENCE DESCRIPTION: SEQ ID NO:9:

```
Xaa  Xaa  Asp  Xaa  Glu  Xaa  Ile  Pro  Glu  Glu  Xaa  Leu  Xaa  Xaa
1                  5                        10
```

( 2 ) INFORMATION FOR SEQ ID NO:10:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=G ( i x ) FEATURE:
    ( A ) NAME/KEY: Modified-site
    ( B ) LOCATION: 2
    ( D ) OTHER INFORMATION: /label=Acc ( i x ) FEATURE:
    ( A ) NAME/KEY: Modified-site
    ( B ) LOCATION: 4
    ( D ) OTHER INFORMATION: /note="Tyr(pPO3H2)"

( i x ) FEATURE:
    ( A ) NAME/KEY: Modified-site
    ( B ) LOCATION: 6
    ( D ) OTHER INFORMATION: /label=Abo ( i x ) FEATURE:
    ( A ) NAME/KEY: Modified-site
    ( B ) LOCATION: 8
    ( D ) OTHER INFORMATION: /label=Oic ( i x ) FEATURE:
    ( A ) NAME/KEY: Modified-site
    ( B ) LOCATION: 11
    ( D ) OTHER INFORMATION: /note="same as c"

( i x ) FEATURE:
    ( A ) NAME/KEY: Modified-site
    ( B ) LOCATION: 13
    ( D ) OTHER INFORMATION: /label=glu ( i x ) FEATURE:
    ( A ) NAME/KEY: Modified-site
    ( B ) LOCATION: 14
    ( D ) OTHER INFORMATION: /note="OH,trifluoroacetate"

( x i ) SEQUENCE DESCRIPTION: SEQ ID NO:10:

```
Xaa  Xaa  Asp  Xaa  Glu  Xaa  Ile  Xaa  Glu  Glu  Xaa  Leu  Xaa  Xaa
1                  5                        10
```

( 2 ) INFORMATION FOR SEQ ID NO:11:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide (ix) FEATURE:
    (A) NAME/KEY: Modified-site
    (B) LOCATION: 1
    (D) OTHER INFORMATION: /label=G (ix) FEATURE:
    (A) NAME/KEY: Modified-site
    (B) LOCATION: 4
    (D) OTHER INFORMATION: /note="Tyr(pPO3H2)"

(ix) FEATURE:
    (A) NAME/KEY: Modified-site
    (B) LOCATION: 6
    (D) OTHER INFORMATION: /label=Abo (ix) FEATURE:
    (A) NAME/KEY: Modified-site
    (B) LOCATION: 8
    (D) OTHER INFORMATION: /label=Oic (ix) FEATURE:
    (A) NAME/KEY: Modified-site
    (B) LOCATION: 11
    (D) OTHER INFORMATION: /note="Tyr(mPO3H2)"

(ix) FEATURE:
    (A) NAME/KEY: Modified-site
    (B) LOCATION: 13
    (D) OTHER INFORMATION: /label=glu (ix) FEATURE:
    (A) NAME/KEY: Modified-site
    (B) LOCATION: 14
    (D) OTHER INFORMATION: /note="OH,trifluoroacetate"

(xi) SEQUENCE DESCRIPTION: SEQ ID NO:11:

Xaa Gly Asp Xaa Glu Xaa Ile Xaa Glu Glu Xaa Leu Xaa Xaa
 1               5                   10

(2) INFORMATION FOR SEQ ID NO:12:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=G (ix) FEATURE:
        (A) NAME/KEY: Modified-site
        (B) LOCATION: 4
        (D) OTHER INFORMATION: /note="Tyr(pPO3H2)"

(ix) FEATURE:
        (A) NAME/KEY: Modified-site
        (B) LOCATION: 6
        (D) OTHER INFORMATION: /label=Abo (ix) FEATURE:
        (A) NAME/KEY: Modified-site
        (B) LOCATION: 11
        (D) OTHER INFORMATION: /note="Tyr(mPO3H2)"

(ix) FEATURE:
        (A) NAME/KEY: Modified-site
        (B) LOCATION: 13
        (D) OTHER INFORMATION: /label=glu (ix) FEATURE:
        (A) NAME/KEY: Modified-site
        (B) LOCATION: 14
        (D) OTHER INFORMATION: /note="OH,trifluoroacetate"

(xi) SEQUENCE DESCRIPTION: SEQ ID NO:12:

```
Xaa Gly Asp Xaa Glu Xaa Ile Pro Glu Glu Xaa Leu Xaa Xaa
1               5                    10
```

( 2 ) INFORMATION FOR SEQ ID NO:13:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=G ( i x ) FEATURE:
        ( A ) NAME/KEY: Modified-site
        ( B ) LOCATION: 4
        ( D ) OTHER INFORMATION: /note="Tyr(pPO3H2)"

( i x ) FEATURE:
        ( A ) NAME/KEY: Modified-site
        ( B ) LOCATION: 6
        ( D ) OTHER INFORMATION: /label=Abo ( i x ) FEATURE:
        ( A ) NAME/KEY: Modified-site
        ( B ) LOCATION: 8
        ( D ) OTHER INFORMATION: /label=Oic ( i x ) FEATURE:
        ( A ) NAME/KEY: Modified-site
        ( B ) LOCATION: 11
        ( D ) OTHER INFORMATION: /note="Tyr(mPO3H2)"

( i x ) FEATURE:
        ( A ) NAME/KEY: Modified-site
        ( B ) LOCATION: 13
        ( D ) OTHER INFORMATION: /label=glu ( i x ) FEATURE:
        ( A ) NAME/KEY: Modified-site
        ( B ) LOCATION: 14
        ( D ) OTHER INFORMATION: /note="OH,trifluoroacetate"

( x i ) SEQUENCE DESCRIPTION: SEQ ID NO:13:

```
Xaa Gly Asp Xaa Glu Xaa Ile Xaa Glu Glu Xaa Leu Xaa Xaa
1               5                    10
```

( 2 ) INFORMATION FOR SEQ ID NO:14:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=G ( i x ) FEATURE:
        ( A ) NAME/KEY: Modified-site
        ( B ) LOCATION: 2
        ( D ) OTHER INFORMATION: /label=Acc ( i x ) FEATURE:
        ( A ) NAME/KEY: Modified-site
        ( B ) LOCATION: 4
        ( D ) OTHER INFORMATION: /note="Tyr(pPO3H2)"

( i x ) FEATURE:

(A) NAME/KEY: Modified-site
        (B) LOCATION: 6
        (D) OTHER INFORMATION: /label=Abo (ix) FEATURE:
        (A) NAME/KEY: Modified-site
        (B) LOCATION: 11
        (D) OTHER INFORMATION: /note="Tyr(mPO3H2)"

(ix) FEATURE:
        (A) NAME/KEY: Modified-site
        (B) LOCATION: 13
        (D) OTHER INFORMATION: /label=glu (ix) FEATURE:
        (A) NAME/KEY: Modified-site
        (B) LOCATION: 14
        (D) OTHER INFORMATION: /note="OH,trifluoroacetate"

(xi) SEQUENCE DESCRIPTION: SEQ ID NO:14:

Xaa Xaa Asp Xaa Glu Xaa Ile Pro Glu Glu Xaa Leu Xaa Xaa
    1               5                   10

(2) INFORMATION FOR SEQ ID NO:15:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=G (ix) FEATURE:
        (A) NAME/KEY: Modified-site
        (B) LOCATION: 2
        (D) OTHER INFORMATION: /label=Acc (ix) FEATURE:
        (A) NAME/KEY: Modified-site
        (B) LOCATION: 6
        (D) OTHER INFORMATION: /label=Abo (ix) FEATURE:
        (A) NAME/KEY: Modified-site
        (B) LOCATION: 11
        (D) OTHER INFORMATION: /note="Phe(pPO3H2)"

(ix) FEATURE:
        (A) NAME/KEY: Modified-site
        (B) LOCATION: 13
        (D) OTHER INFORMATION: /label=glu (ix) FEATURE:
        (A) NAME/KEY: Modified-site
        (B) LOCATION: 14
        (D) OTHER INFORMATION: /note="OH,trifluoroacetate"

(xi) SEQUENCE DESCRIPTION: SEQ ID NO:15:

Xaa Xaa Asp Phe Glu Xaa Ile Pro Glu Glu Xaa Leu Xaa Xaa
    1               5                   10

(2) INFORMATION FOR SEQ ID NO:16:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:

-continued (A) NAME/KEY: Modified-site
                (B) LOCATION: 1
                (D) OTHER INFORMATION: /label=G (ix) FEATURE:
                (A) NAME/KEY: Modified-site
                (B) LOCATION: 6
                (D) OTHER INFORMATION: /label=Abo (ix) FEATURE:
                (A) NAME/KEY: Modified-site
                (B) LOCATION: 8
                (D) OTHER INFORMATION: /label=Oic (ix) FEATURE:
                (A) NAME/KEY: Modified-site
                (B) LOCATION: 11
                (D) OTHER INFORMATION: /note="Phe(pPO3H2)"

(ix) FEATURE:
                (A) NAME/KEY: Modified-site
                (B) LOCATION: 13
                (D) OTHER INFORMATION: /label=glu (ix) FEATURE:
                (A) NAME/KEY: Modified-site
                (B) LOCATION: 14
                (D) OTHER INFORMATION: /note="OH,trifluoroacetate"

(xi) SEQUENCE DESCRIPTION: SEQ ID NO:16:

Xaa  Gly  Asp  Phe  Glu  Xaa  Ile  Xaa  Glu  Glu  Xaa  Leu  Xaa  Xaa
    1                   5                        10

(2) INFORMATION FOR SEQ ID NO:17:

(i) SEQUENCE CHARACTERISTICS:
                (A) LENGTH: 14 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /label=G (ix) FEATURE:
                (A) NAME/KEY: Modified-site
                (B) LOCATION: 6
                (D) OTHER INFORMATION: /label=Abo (ix) FEATURE:
                (A) NAME/KEY: Modified-site
                (B) LOCATION: 11
                (D) OTHER INFORMATION: /note="Phe(pPO3H2)"

(ix) FEATURE:
                (A) NAME/KEY: Modified-site
                (B) LOCATION: 13
                (D) OTHER INFORMATION: /label=glu (ix) FEATURE:
                (A) NAME/KEY: Modified-site
                (B) LOCATION: 14
                (D) OTHER INFORMATION: /note="OH,trifluoroacetate"

(xi) SEQUENCE DESCRIPTION: SEQ ID NO:17:

Xaa  Gly  Asp  Phe  Glu  Xaa  Ile  Pro  Glu  Glu  Xaa  Leu  Xaa  Xaa
    1                   5                        10

(2) INFORMATION FOR SEQ ID NO:18:

(i) SEQUENCE CHARACTERISTICS:
                (A) LENGTH: 14 amino acids
                (B) TYPE: amino acid
                (C) STRANDEDNESS: single -continued ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=G ( i x ) FEATURE:
        ( A ) NAME/KEY: Modified-site
        ( B ) LOCATION: 2
        ( D ) OTHER INFORMATION: /label=Acc ( i x ) FEATURE:
        ( A ) NAME/KEY: Modified-site
        ( B ) LOCATION: 6
        ( D ) OTHER INFORMATION: /label=Abo ( i x ) FEATURE:
        ( A ) NAME/KEY: Modified-site
        ( B ) LOCATION: 8
        ( D ) OTHER INFORMATION: /label=Oic ( i x ) FEATURE:
        ( A ) NAME/KEY: Modified-site
        ( B ) LOCATION: 11
        ( D ) OTHER INFORMATION: /note="Phe(pPO3H2)"

( i x ) FEATURE:
        ( A ) NAME/KEY: Modified-site
        ( B ) LOCATION: 13
        ( D ) OTHER INFORMATION: /label=glu ( i x ) FEATURE:
        ( A ) NAME/KEY: Modified-site
        ( B ) LOCATION: 14
        ( D ) OTHER INFORMATION: /note="OH,trifluoroacetate"

( x i ) SEQUENCE DESCRIPTION: SEQ ID NO:18:

Xaa Xaa Asp Phe Glu Xaa Ile Xaa Glu Glu Xaa Leu Xaa Xaa
1                  5                                  10

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=G ( i x ) FEATURE:
        ( A ) NAME/KEY: Modified-site
        ( B ) LOCATION: 2
        ( D ) OTHER INFORMATION: /label=Acc ( i x ) FEATURE:
        ( A ) NAME/KEY: Modified-site
        ( B ) LOCATION: 4
        ( D ) OTHER INFORMATION: /note="Phe(pPO3H2)"

( i x ) FEATURE:
        ( A ) NAME/KEY: Modified-site
        ( B ) LOCATION: 6
        ( D ) OTHER INFORMATION: /label=Abo ( i x ) FEATURE:
        ( A ) NAME/KEY: Modified-site
        ( B ) LOCATION: 11
        ( D ) OTHER INFORMATION: /note="Phe(pPO3H2)"

( i x ) FEATURE:
        ( A ) NAME/KEY: Modified-site (B) LOCATION: 13
(D) OTHER INFORMATION: /label=glu (ix) FEATURE:
(A) NAME/KEY: Modified-site
(B) LOCATION: 14
(D) OTHER INFORMATION: /note="OH,trifluoroacetate"

(xi) SEQUENCE DESCRIPTION: SEQ ID NO:19:

Xaa Xaa Asp Xaa Glu Xaa Ile Pro Glu Glu Xaa Leu Xaa Xaa
1               5                   10

(2) INFORMATION FOR SEQ ID NO:20:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=G (ix) FEATURE:
(A) NAME/KEY: Modified-site
(B) LOCATION: 2
(D) OTHER INFORMATION: /label=Acc (ix) FEATURE:
(A) NAME/KEY: Modified-site
(B) LOCATION: 4
(D) OTHER INFORMATION: /note="Phe(pPO3H2)"

(ix) FEATURE:
(A) NAME/KEY: Modified-site
(B) LOCATION: 6
(D) OTHER INFORMATION: /label=Abo (ix) FEATURE:
(A) NAME/KEY: Modified-site
(B) LOCATION: 8
(D) OTHER INFORMATION: /label=Oic (ix) FEATURE:
(A) NAME/KEY: Modified-site
(B) LOCATION: 11
(D) OTHER INFORMATION: /note="Phe(pPO3H2)"

(ix) FEATURE:
(A) NAME/KEY: Modified-site
(B) LOCATION: 13
(D) OTHER INFORMATION: /label=glu (ix) FEATURE:
(A) NAME/KEY: Modified-site
(B) LOCATION: 14
(D) OTHER INFORMATION: /note="OH,trifluoroacetate"

(xi) SEQUENCE DESCRIPTION: SEQ ID NO:20:

Xaa Xaa Asp Xaa Glu Xaa Ile Xaa Glu Glu Xaa Leu Xaa Xaa
1               5                   10

(2) INFORMATION FOR SEQ ID NO:21:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site (B) LOCATION: 1
(D) OTHER INFORMATION: /label=G (ix) FEATURE:
(A) NAME/KEY: Modified-site
(B) LOCATION: 4
(D) OTHER INFORMATION: /note="Phe(pPO3H2)"

(ix) FEATURE:
(A) NAME/KEY: Modified-site
(B) LOCATION: 6
(D) OTHER INFORMATION: /label=Abo (ix) FEATURE:
(A) NAME/KEY: Modified-site
(B) LOCATION: 8
(D) OTHER INFORMATION: /label=Oic (ix) FEATURE:
(A) NAME/KEY: Modified-site
(B) LOCATION: 11
(D) OTHER INFORMATION: /note="Phe(pPO3H2)"

(ix) FEATURE:
(A) NAME/KEY: Modified-site
(B) LOCATION: 13
(D) OTHER INFORMATION: /label=glu (ix) FEATURE:
(A) NAME/KEY: Modified-site
(B) LOCATION: 14
(D) OTHER INFORMATION: /note="OH,trifluoroacetate"

(xi) SEQUENCE DESCRIPTION: SEQ ID NO:21:

Xaa Gly Asp Xaa Glu Xaa Ile Xaa Glu Glu Xaa Leu Xaa Xaa
1               5                   10

(2) INFORMATION FOR SEQ ID NO:22:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X0

(ix) FEATURE:
(A) NAME/KEY: Modified-site
(B) LOCATION: 6
(D) OTHER INFORMATION: /label=Abo (ix) FEATURE:
(A) NAME/KEY: Modified-site
(B) LOCATION: 11
(D) OTHER INFORMATION: /note="Tyr(pPO3H2)"

(ix) FEATURE:
(A) NAME/KEY: Modified-site
(B) LOCATION: 13
(D) OTHER INFORMATION: /label=glu (ix) FEATURE:
(A) NAME/KEY: Modified-site
(B) LOCATION: 14
(D) OTHER INFORMATION: /note="OH,trifluoroacetate"

(xi) SEQUENCE DESCRIPTION: SEQ ID NO:22:

Xaa Gly Asp Tyr Glu Xaa Ile Pro Glu Glu Xaa Leu Xaa Xaa
1               5                   10

(2) INFORMATION FOR SEQ ID NO:23:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /label=X0

( i x ) FEATURE:
  ( A ) NAME/KEY: Modified-site
  ( B ) LOCATION: 6
  ( D ) OTHER INFORMATION: /label=Abo ( i x ) FEATURE:
  ( A ) NAME/KEY: Modified-site
  ( B ) LOCATION: 8
  ( D ) OTHER INFORMATION: /label=Oic ( i x ) FEATURE:
  ( A ) NAME/KEY: Modified-site
  ( B ) LOCATION: 11
  ( D ) OTHER INFORMATION: /note="Tyr(pPO3H2)"

( i x ) FEATURE:
  ( A ) NAME/KEY: Modified-site
  ( B ) LOCATION: 13
  ( D ) OTHER INFORMATION: /label=glu ( i x ) FEATURE:
  ( A ) NAME/KEY: Modified-site
  ( B ) LOCATION: 14
  ( D ) OTHER INFORMATION: /note="OH,trifluoroacetate"

( x i ) SEQUENCE DESCRIPTION: SEQ ID NO:23:

Xaa Gly Asp Tyr Glu Xaa Ile Xaa Glu Glu Xaa Leu Xaa Xaa
1               5                   10

( 2 ) INFORMATION FOR SEQ ID NO:24:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=X0

( i x ) FEATURE:
    ( A ) NAME/KEY: Modified-site
    ( B ) LOCATION: 2
    ( D ) OTHER INFORMATION: /label=Acc ( i x ) FEATURE:
    ( A ) NAME/KEY: Modified-site
    ( B ) LOCATION: 6
    ( D ) OTHER INFORMATION: /label=Abo ( i x ) FEATURE:
    ( A ) NAME/KEY: Modified-site
    ( B ) LOCATION: 11
    ( D ) OTHER INFORMATION: /note="Tyr(pPO3H2)"

( i x ) FEATURE:
    ( A ) NAME/KEY: Modified-site
    ( B ) LOCATION: 13
    ( D ) OTHER INFORMATION: /label=glu ( i x ) FEATURE:
    ( A ) NAME/KEY: Modified-site
    ( B ) LOCATION: 14

(D) OTHER INFORMATION: /note="OH,trifluoroacetate"

(x i) SEQUENCE DESCRIPTION: SEQ ID NO:24:

Xaa Xaa Asp Tyr Glu Xaa Ile Pro Glu Glu Xaa Leu Xaa Xaa
1               5                   10

(2) INFORMATION FOR SEQ ID NO:25:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /label=X2

(i x) FEATURE:
        (A) NAME/KEY: Modified-site
        (B) LOCATION: 6
        (D) OTHER INFORMATION: /label=Abo (i x) FEATURE:
        (A) NAME/KEY: Modified-site
        (B) LOCATION: 8
        (D) OTHER INFORMATION: /label=Pip (i x) FEATURE:
        (A) NAME/KEY: Modified-site
        (B) LOCATION: 11
        (D) OTHER INFORMATION: /note="Tyr(mPO3H2)"

(i x) FEATURE:
        (A) NAME/KEY: Modified-site
        (B) LOCATION: 13
        (D) OTHER INFORMATION: /note="OH,trifluoroacetate"

(x i) SEQUENCE DESCRIPTION: SEQ ID NO:25:

Xaa Gly Asp Phe Glu Xaa Ile Xaa Glu Glu Xaa Leu Xaa
1               5                   10

(2) INFORMATION FOR SEQ ID NO:26:

(i) SEQUENCE CHARACTERISTICS:
        (A) LENGTH: 14 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /label=X3

(i x) FEATURE:
        (A) NAME/KEY: Modified-site
        (B) LOCATION: 6
        (D) OTHER INFORMATION: /label=Abo (i x) FEATURE:
        (A) NAME/KEY: Modified-site
        (B) LOCATION: 11
        (D) OTHER INFORMATION: /note="Tyr(mPO3H2)"

(i x) FEATURE:
        (A) NAME/KEY: Modified-site
        (B) LOCATION: 13
        (D) OTHER INFORMATION: /label=glu (i x) FEATURE:
        (A) NAME/KEY: Modified-site
        (B) LOCATION: 14

(D) OTHER INFORMATION: /note="OH,trifluoroacetate"

(xi) SEQUENCE DESCRIPTION: SEQ ID NO:26:

Xaa Gly Asp Phe Glu Xaa Ile Pro Glu Glu Xaa Leu Xaa Xaa
1               5                   10

(2) INFORMATION FOR SEQ ID NO:27:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=G (ix) FEATURE:
        (A) NAME/KEY: Modified-site
        (B) LOCATION: 6
        (D) OTHER INFORMATION: /label=Abo (ix) FEATURE:
        (A) NAME/KEY: Modified-site
        (B) LOCATION: 8
        (D) OTHER INFORMATION: /label=Pip (ix) FEATURE:
        (A) NAME/KEY: Modified-site
        (B) LOCATION: 11
        (D) OTHER INFORMATION: /note="Tyr(mPO3H2)"

(ix) FEATURE:
        (A) NAME/KEY: Modified-site
        (B) LOCATION: 13
        (D) OTHER INFORMATION: /label=bAla (ix) FEATURE:
        (A) NAME/KEY: Modified-site
        (B) LOCATION: 14
        (D) OTHER INFORMATION: /note="OH,trifluoroacetate"

(xi) SEQUENCE DESCRIPTION: SEQ ID NO:27:

Xaa Gly Asp Phe Glu Xaa Ile Xaa Glu Glu Xaa Leu Xaa Xaa
1               5                   10

(2) INFORMATION FOR SEQ ID NO:28:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=G (ix) FEATURE:
        (A) NAME/KEY: Modified-site
        (B) LOCATION: 6
        (D) OTHER INFORMATION: /label=Abo (ix) FEATURE:
        (A) NAME/KEY: Modified-site
        (B) LOCATION: 8
        (D) OTHER INFORMATION: /label=Pip (ix) FEATURE:
        (A) NAME/KEY: Modified-site
        (B) LOCATION: 11

-continued ( D ) OTHER INFORMATION: /note="Tyr(mPO3H2)"

( i x ) FEATURE:
                ( A ) NAME/KEY: Modified-site
                ( B ) LOCATION: 13
                ( D ) OTHER INFORMATION: /label=4Abu ( i x ) FEATURE:
                ( A ) NAME/KEY: Modified-site
                ( B ) LOCATION: 14
                ( D ) OTHER INFORMATION: /note="OH,trifluoroacetate"

( x i ) SEQUENCE DESCRIPTION: SEQ ID NO:28:

Xaa  Gly  Asp  Phe  Glu  Xaa  Ile  Xaa  Glu  Glu  Xaa  Leu  Xaa  Xaa
    1                   5                        10

( 2 ) INFORMATION FOR SEQ ID NO:29:

( i ) SEQUENCE CHARACTERISTICS:
                ( A ) LENGTH: 12 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Modified-site
                ( B ) LOCATION: 1
                ( D ) OTHER INFORMATION: /label=G ( i x ) FEATURE:
                ( A ) NAME/KEY: Modified-site
                ( B ) LOCATION: 4
                ( D ) OTHER INFORMATION: /label=Abo ( i x ) FEATURE:
                ( A ) NAME/KEY: Modified-site
                ( B ) LOCATION: 9
                ( D ) OTHER INFORMATION: /note="Tyr(mPO3H2)"

( i x ) FEATURE:
                ( A ) NAME/KEY: Modified-site
                ( B ) LOCATION: 11
                ( D ) OTHER INFORMATION: /label=glu ( i x ) FEATURE:
                ( A ) NAME/KEY: Modified-site
                ( B ) LOCATION: 12
                ( D ) OTHER INFORMATION: /note="OH,trifluoroacetate"

( x i ) SEQUENCE DESCRIPTION: SEQ ID NO:29:

Xaa  Phe  Glu  Xaa  Ile  Pro  Glu  Glu  Xaa  Leu  Xaa  Xaa
    1                   5                        10

( 2 ) INFORMATION FOR SEQ ID NO:30:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Modified-site
                ( B ) LOCATION: 1
                ( D ) OTHER INFORMATION: /label=G ( i x ) FEATURE:
                ( A ) NAME/KEY: Modified-site
                ( B ) LOCATION: 3
                ( D ) OTHER INFORMATION: /label=Abo ( i x ) FEATURE:
                ( A ) NAME/KEY: Modified-site
                ( B ) LOCATION: 8

-continued ( D ) OTHER INFORMATION: /note="Tyr(mPO3H2)"

( i x ) FEATURE:
            ( A ) NAME/KEY: Modified-site
            ( B ) LOCATION: 10
            ( D ) OTHER INFORMATION: /label=glu ( i x ) FEATURE:
            ( A ) NAME/KEY: Modified-site
            ( B ) LOCATION: 11
            ( D ) OTHER INFORMATION: /note="OH,trifluoroacetate"

( x i ) SEQUENCE DESCRIPTION: SEQ ID NO:30:

Xaa  Glu  Xaa  Ile  Pro  Glu  Glu  Xaa  Leu  Xaa  Xaa
    1                  5                            10

( 2 ) INFORMATION FOR SEQ ID NO:31:

( i ) SEQUENCE CHARACTERISTICS:
            ( A ) LENGTH: 12 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /label=G ( i x ) FEATURE:
            ( A ) NAME/KEY: Modified-site
            ( B ) LOCATION: 4
            ( D ) OTHER INFORMATION: /label=Abo ( i x ) FEATURE:
            ( A ) NAME/KEY: Modified-site
            ( B ) LOCATION: 9
            ( D ) OTHER INFORMATION: /note="Tyr(pPO3H2)"

( i x ) FEATURE:
            ( A ) NAME/KEY: Modified-site
            ( B ) LOCATION: 11
            ( D ) OTHER INFORMATION: /label=bAla ( i x ) FEATURE:
            ( A ) NAME/KEY: Modified-site
            ( B ) LOCATION: 12
            ( D ) OTHER INFORMATION: /note="OH,trifluoroacetate"

( x i ) SEQUENCE DESCRIPTION: SEQ ID NO:31:

Xaa  Phe  Glu  Xaa  Ile  Pro  Glu  Glu  Xaa  Leu  Xaa  Xaa
    1                       5                            10

( 2 ) INFORMATION FOR SEQ ID NO:32:

( i ) SEQUENCE CHARACTERISTICS:
            ( A ) LENGTH: 12 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /label=G ( i x ) FEATURE:
            ( A ) NAME/KEY: Modified-site
            ( B ) LOCATION: 4
            ( D ) OTHER INFORMATION: /label=Abo ( i x ) FEATURE:
            ( A ) NAME/KEY: Modified-site
            ( B ) LOCATION: 9

( D ) OTHER INFORMATION: /note="Phe(pPO3H2)"

( i x ) FEATURE:
    ( A ) NAME/KEY: Modified-site
    ( B ) LOCATION: 11
    ( D ) OTHER INFORMATION: /label=glu ( i x ) FEATURE:
    ( A ) NAME/KEY: Modified-site
    ( B ) LOCATION: 12
    ( D ) OTHER INFORMATION: /note="OH,trifluoroacetate"

( x i ) SEQUENCE DESCRIPTION: SEQ ID NO:32:

Xaa Phe Glu Xaa Ile Pro Glu Glu Xaa Leu Xaa Xaa
1           5                   10

( 2 ) INFORMATION FOR SEQ ID NO:33:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=G ( i x ) FEATURE:
    ( A ) NAME/KEY: Modified-site
    ( B ) LOCATION: 2
    ( D ) OTHER INFORMATION: /label=Acc ( i x ) FEATURE:
    ( A ) NAME/KEY: Modified-site
    ( B ) LOCATION: 6
    ( D ) OTHER INFORMATION: /label=Abo ( i x ) FEATURE:
    ( A ) NAME/KEY: Modified-site
    ( B ) LOCATION: 11
    ( D ) OTHER INFORMATION: /note="Phe(pCH2CO2H)"

( i x ) FEATURE:
    ( A ) NAME/KEY: Modified-site
    ( B ) LOCATION: 13
    ( D ) OTHER INFORMATION: /label=glu ( i x ) FEATURE:
    ( A ) NAME/KEY: Modified-site
    ( B ) LOCATION: 14
    ( D ) OTHER INFORMATION: /note="OH,trifluoroacetate"

( x i ) SEQUENCE DESCRIPTION: SEQ ID NO:33:

Xaa Xaa Asp Phe Glu Xaa Ile Pro Glu Glu Xaa Leu Xaa Xaa
1           5                   10

( 2 ) INFORMATION FOR SEQ ID NO:34:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=G ( i x ) FEATURE:
    ( A ) NAME/KEY: Modified-site
    ( B ) LOCATION: 6

(D) OTHER INFORMATION: /label=Abo (ix) FEATURE:
    (A) NAME/KEY: Modified-site
    (B) LOCATION: 11
    (D) OTHER INFORMATION: /note="Phe(pCH2CO2H)"

(ix) FEATURE:
    (A) NAME/KEY: Modified-site
    (B) LOCATION: 13
    (D) OTHER INFORMATION: /label=glu (ix) FEATURE:
    (A) NAME/KEY: Modified-site
    (B) LOCATION: 14
    (D) OTHER INFORMATION: /note="OH,trifluoroacetate"

(xi) SEQUENCE DESCRIPTION: SEQ ID NO:34:

Xaa Gly Asp Phe Glu Xaa Ile Pro Glu Glu Xaa Leu Xaa Xaa
1               5                   10

(2) INFORMATION FOR SEQ ID NO:35:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=G (ix) FEATURE:
        (A) NAME/KEY: Modified-site
        (B) LOCATION: 6
        (D) OTHER INFORMATION: /label=Abo (ix) FEATURE:
        (A) NAME/KEY: Modified-site
        (B) LOCATION: 11
        (D) OTHER INFORMATION: /note="phe(pCH2CO2H)"

(ix) FEATURE:
        (A) NAME/KEY: Modified-site
        (B) LOCATION: 13
        (D) OTHER INFORMATION: /label=glu (ix) FEATURE:
        (A) NAME/KEY: Modified-site
        (B) LOCATION: 14
        (D) OTHER INFORMATION: /note="OH,trifluoroacetate"

(xi) SEQUENCE DESCRIPTION: SEQ ID NO:35:

Xaa Gly Asp Phe Glu Xaa Ile Pro Glu Glu Xaa Leu Xaa Xaa
1               5                   10

(2) INFORMATION FOR SEQ ID NO:36:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=G (ix) FEATURE:
        (A) NAME/KEY: Modified-site
        (B) LOCATION: 2

( D ) OTHER INFORMATION: /label=Acc ( i x ) FEATURE:
 ( A ) NAME/KEY: Modified-site
 ( B ) LOCATION: 6
 ( D ) OTHER INFORMATION: /label=Abo ( i x ) FEATURE:
 ( A ) NAME/KEY: Modified-site
 ( B ) LOCATION: 8
 ( D ) OTHER INFORMATION: /label=Oic ( i x ) FEATURE:
 ( A ) NAME/KEY: Modified-site
 ( B ) LOCATION: 11
 ( D ) OTHER INFORMATION: /note="Phe(pCH2CO2H)"

( i x ) FEATURE:
 ( A ) NAME/KEY: Modified-site
 ( B ) LOCATION: 13
 ( D ) OTHER INFORMATION: /label=glu ( i x ) FEATURE:
 ( A ) NAME/KEY: Modified-site
 ( B ) LOCATION: 14
 ( D ) OTHER INFORMATION: /note="OH,trifluoroacetate"

( x i ) SEQUENCE DESCRIPTION: SEQ ID NO:36:

Xaa Xaa Asp Phe Glu Xaa Ile Xaa Glu Glu Xaa Leu Xaa Xaa
1     5        10

( 2 ) INFORMATION FOR SEQ ID NO:37:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /label=G ( i x ) FEATURE:
  ( A ) NAME/KEY: Modified-site
  ( B ) LOCATION: 6
  ( D ) OTHER INFORMATION: /label=Abo ( i x ) FEATURE:
  ( A ) NAME/KEY: Modified-site
  ( B ) LOCATION: 8
  ( D ) OTHER INFORMATION: /label=Oic ( i x ) FEATURE:
  ( A ) NAME/KEY: Modified-site
  ( B ) LOCATION: 11
  ( D ) OTHER INFORMATION: /note="Phe(pCH2CO2H)"

( i x ) FEATURE:
  ( A ) NAME/KEY: Modified-site
  ( B ) LOCATION: 13
  ( D ) OTHER INFORMATION: /label=glu ( i x ) FEATURE:
  ( A ) NAME/KEY: Modified-site
  ( B ) LOCATION: 14
  ( D ) OTHER INFORMATION: /note="OH,trifluoroacetate"

( x i ) SEQUENCE DESCRIPTION: SEQ ID NO:37:

Xaa Gly Asp Phe Glu Xaa Ile Xaa Glu Glu Xaa Leu Xaa Xaa
1     5        10

( 2 ) INFORMATION FOR SEQ ID NO:38:

( i ) SEQUENCE CHARACTERISTICS:

(A) LENGTH: 14 amino acids
(B) TYPE: amino acid
(C) STRANDEDNESS: single
(D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=G (ix) FEATURE:
    (A) NAME/KEY: Modified-site
    (B) LOCATION: 6
    (D) OTHER INFORMATION: /label=Abo (ix) FEATURE:
    (A) NAME/KEY: Modified-site
    (B) LOCATION: 8
    (D) OTHER INFORMATION: /label=Pip (ix) FEATURE:
    (A) NAME/KEY: Modified-site
    (B) LOCATION: 11
    (D) OTHER INFORMATION: /note="Phe(pCH2CO2H)"

(ix) FEATURE:
    (A) NAME/KEY: Modified-site
    (B) LOCATION: 13
    (D) OTHER INFORMATION: /label=glu (ix) FEATURE:
    (A) NAME/KEY: Modified-site
    (B) LOCATION: 14
    (D) OTHER INFORMATION: /note="OH,trifluoroacetate"

(xi) SEQUENCE DESCRIPTION: SEQ ID NO:38:

Xaa Gly Asp Phe Glu Xaa Ile Xaa Glu Glu Xaa Leu Xaa Xaa
1               5                   10

(2) INFORMATION FOR SEQ ID NO:39:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=X0

(ix) FEATURE:
    (A) NAME/KEY: Modified-site
    (B) LOCATION: 2
    (D) OTHER INFORMATION: /label=Acc (ix) FEATURE:
    (A) NAME/KEY: Modified-site
    (B) LOCATION: 6
    (D) OTHER INFORMATION: /label=Abo (ix) FEATURE:
    (A) NAME/KEY: Modified-site
    (B) LOCATION: 8
    (D) OTHER INFORMATION: /label=Oic (ix) FEATURE:
    (A) NAME/KEY: Modified-site
    (B) LOCATION: 11
    (D) OTHER INFORMATION: /note="Phe(pCH2CO2H)"

(ix) FEATURE:
    (A) NAME/KEY: Modified-site
    (B) LOCATION: 13
    (D) OTHER INFORMATION: /label=glu (ix) FEATURE:
  (A) NAME/KEY: Modified-site
  (B) LOCATION: 14
  (D) OTHER INFORMATION: /note="OH,trifluoroacetate"

(xi) SEQUENCE DESCRIPTION: SEQ ID NO:39:

Xaa Xaa Asp Phe Glu Xaa Ile Xaa Glu Glu Xaa Leu Xaa Xaa
1               5                   10

(2) INFORMATION FOR SEQ ID NO:40:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=X0

(ix) FEATURE:
    (A) NAME/KEY: Modified-site
    (B) LOCATION: 2
    (D) OTHER INFORMATION: /label=Acc (ix) FEATURE:
    (A) NAME/KEY: Modified-site
    (B) LOCATION: 6
    (D) OTHER INFORMATION: /label=Abo (ix) FEATURE:
    (A) NAME/KEY: Modified-site
    (B) LOCATION: 8
    (D) OTHER INFORMATION: /label=Pip (ix) FEATURE:
    (A) NAME/KEY: Modified-site
    (B) LOCATION: 11
    (D) OTHER INFORMATION: /note="Phe(pCH2CO2H)"

(ix) FEATURE:
    (A) NAME/KEY: Modified-site
    (B) LOCATION: 13
    (D) OTHER INFORMATION: /label=glu (ix) FEATURE:
    (A) NAME/KEY: Modified-site
    (B) LOCATION: 14
    (D) OTHER INFORMATION: /note="OH,trifluoroacetate"

(xi) SEQUENCE DESCRIPTION: SEQ ID NO:40:

Xaa Xaa Asp Phe Glu Xaa Ile Xaa Glu Glu Xaa Leu Xaa Xaa
1               5                   10

(2) INFORMATION FOR SEQ ID NO:41:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=X2

(ix) FEATURE:
    (A) NAME/KEY: Modified-site
    (B) LOCATION: 2
    (D) OTHER INFORMATION: /label=Acc ( i x ) FEATURE:
    ( A ) NAME/KEY: Modified-site
    ( B ) LOCATION: 6
    ( D ) OTHER INFORMATION: /label=Abo ( i x ) FEATURE:
    ( A ) NAME/KEY: Modified-site
    ( B ) LOCATION: 8
    ( D ) OTHER INFORMATION: /label=Abo ( i x ) FEATURE:
    ( A ) NAME/KEY: Modified-site
    ( B ) LOCATION: 11
    ( D ) OTHER INFORMATION: /note="Phe(pCH2CO2H)"

( i x ) FEATURE:
    ( A ) NAME/KEY: Modified-site
    ( B ) LOCATION: 13
    ( D ) OTHER INFORMATION: /label=glu ( i x ) FEATURE:
    ( A ) NAME/KEY: Modified-site
    ( B ) LOCATION: 14
    ( D ) OTHER INFORMATION: /note="OH,trifluoroacetate"

( x i ) SEQUENCE DESCRIPTION: SEQ ID NO:41:

Xaa Xaa Asp Phe Glu Xaa Ile Xaa Glu Glu Xaa Leu Xaa Xaa
1               5                   10

( 2 ) INFORMATION FOR SEQ ID NO:42:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=X3

( i x ) FEATURE:
    ( A ) NAME/KEY: Modified-site
    ( B ) LOCATION: 2
    ( D ) OTHER INFORMATION: /label=Acc ( i x ) FEATURE:
    ( A ) NAME/KEY: Modified-site
    ( B ) LOCATION: 6
    ( D ) OTHER INFORMATION: /label=Abo ( i x ) FEATURE:
    ( A ) NAME/KEY: Modified-site
    ( B ) LOCATION: 8
    ( D ) OTHER INFORMATION: /label=Abo ( i x ) FEATURE:
    ( A ) NAME/KEY: Modified-site
    ( B ) LOCATION: 11
    ( D ) OTHER INFORMATION: /note="Phe(pCH2CO2H)"

( i x ) FEATURE:
    ( A ) NAME/KEY: Modified-site
    ( B ) LOCATION: 13
    ( D ) OTHER INFORMATION: /label=glu ( i x ) FEATURE:
    ( A ) NAME/KEY: Modified-site
    ( B ) LOCATION: 14
    ( D ) OTHER INFORMATION: /note="OH,trifluoroacetate"

( x i ) SEQUENCE DESCRIPTION: SEQ ID NO:42:

Xaa Xaa Asp Phe Glu Xaa Ile Xaa Glu Glu Xaa Leu Xaa Xaa
1               5                   10

( 2 ) INFORMATION FOR SEQ ID NO:43:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X3

( i x ) FEATURE:
        ( A ) NAME/KEY: Modified-site
        ( B ) LOCATION: 2
        ( D ) OTHER INFORMATION: /label=Acc ( i x ) FEATURE:
        ( A ) NAME/KEY: Modified-site
        ( B ) LOCATION: 6
        ( D ) OTHER INFORMATION: /label=Abo ( i x ) FEATURE:
        ( A ) NAME/KEY: Modified-site
        ( B ) LOCATION: 8
        ( D ) OTHER INFORMATION: /label=Pip ( i x ) FEATURE:
        ( A ) NAME/KEY: Modified-site
        ( B ) LOCATION: 11
        ( D ) OTHER INFORMATION: /note="Phe(pCH2CO2H)"

( i x ) FEATURE:
        ( A ) NAME/KEY: Modified-site
        ( B ) LOCATION: 13
        ( D ) OTHER INFORMATION: /label=glu ( i x ) FEATURE:
        ( A ) NAME/KEY: Modified-site
        ( B ) LOCATION: 14
        ( D ) OTHER INFORMATION: /note="OH,trifluoroacetate"

( x i ) SEQUENCE DESCRIPTION: SEQ ID NO:43:

```
Xaa  Xaa  Asp  Phe  Glu  Xaa  Ile  Xaa  Glu  Glu  Xaa  Leu  Xaa  Xaa
 1                  5                            10
```

( 2 ) INFORMATION FOR SEQ ID NO:44:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=G ( i x ) FEATURE:
        ( A ) NAME/KEY: Modified-site
        ( B ) LOCATION: 2
        ( D ) OTHER INFORMATION: /label=Acc ( i x ) FEATURE:
        ( A ) NAME/KEY: Modified-site
        ( B ) LOCATION: 6
        ( D ) OTHER INFORMATION: /label=Abo ( i x ) FEATURE:
        ( A ) NAME/KEY: Modified-site
        ( B ) LOCATION: 8
        ( D ) OTHER INFORMATION: /label=Pip -continued

```
( i x ) FEATURE:
          ( A ) NAME/KEY: Modified-site
          ( B ) LOCATION: 11
          ( D ) OTHER INFORMATION: /note="Phe(pCH2CO2H)"

( i x ) FEATURE:
          ( A ) NAME/KEY: Modified-site
          ( B ) LOCATION: 13
          ( D ) OTHER INFORMATION: /label=glu ( i x ) FEATURE:
          ( A ) NAME/KEY: Modified-site
          ( B ) LOCATION: 14
          ( D ) OTHER INFORMATION: /note="OH,trifluoroacetate"

( x i ) SEQUENCE DESCRIPTION: SEQ ID NO:44:

Xaa  Xaa  Asp  Phe  Glu  Xaa  Ile  Xaa  Glu  Glu  Xaa  Leu  Xaa  Xaa
 1              5                        10
```